United States Patent
Victor et al.

(10) Patent No.: US 11,130,111 B2
(45) Date of Patent: *Sep. 28, 2021

(54) AIR-COOLED HEAT EXCHANGERS

(71) Applicant: UOP LLC, Des Plaines, IL (US)

(72) Inventors: Sanford Allan Victor, Buffalo Grove, IL (US); Phillip F. Daly, Palatine, IL (US); Ian G. Horn, Streamwood, IL (US)

(73) Assignee: UOP LLC, Des Plaines, IL (US)

( * ) Notice: Subject to any disclaimer, the term of this patent is extended or adjusted under 35 U.S.C. 154(b) by 221 days.

This patent is subject to a terminal disclaimer.

(21) Appl. No.: 15/937,602

(22) Filed: Mar. 27, 2018

(65) Prior Publication Data

US 2018/0280917 A1 Oct. 4, 2018

Related U.S. Application Data

(60) Provisional application No. 62/477,729, filed on Mar. 28, 2017.

(51) Int. Cl.
*B01J 19/00* (2006.01)
*F28F 27/00* (2006.01)
(Continued)

(52) U.S. Cl.
CPC ............ *B01J 19/0006* (2013.01); *B01J 8/26* (2013.01); *B01J 19/0033* (2013.01);
(Continued)

(58) Field of Classification Search
CPC .......... B01J 19/0006; B01J 2219/00058; B01J 2219/00069; B01J 2219/00268;
(Continued)

(56) References Cited

U.S. PATENT DOCUMENTS

| 4,159,239 A | 6/1979 | Schwartz ...................... 208/113 |
| 4,267,458 A | 5/1981 | Uram .......................... 290/40 R |

(Continued)

FOREIGN PATENT DOCUMENTS

| EP | 0181744 A1 | 5/1986 | ............ B65G 53/66 |
| EP | 2746884 A1 | 6/2014 | ............ G05B 23/02 |

(Continued)

OTHER PUBLICATIONS

Seth, "Process Heat Transfer Principles and Applications: 12 Air-Cooled Heat Exchangers", 2007, Elsevier Ltd, pp. 629-680. downloaded from the internet https://pdf.sciencedirectassets.com . . . (Year: 2007).*

(Continued)

*Primary Examiner* — Rocio Del Mar Perez-Velez
*Assistant Examiner* — Olvin Lopez Alvarez

(57) ABSTRACT

A plant or refinery may include equipment such as reactors, heaters, heat exchangers, regenerators, separators, or the like. Types of heat exchangers include shell and tube, plate, plate and shell, plate fin, air cooled, wetted-surface air cooled, or the like. Operating methods may impact deterioration in equipment condition, prolong equipment life, extend production operating time, or provide other benefits. Mechanical or digital sensors may be used for monitoring equipment, and sensor data may be programmatically analyzed to identify developing problems. For example, sensors may be used in conjunction with one or more system components to detect and correct maldistribution, cross-leakage, strain, pre-leakage, thermal stresses, fouling, vibration, problems in liquid lifting, conditions that can affect air-cooled exchangers, conditions that can affect a wetted-surface air-cooled heat exchanger, or the like. An operating condition or mode may be adjusted to prolong equipment life or avoid equipment failure.

17 Claims, 14 Drawing Sheets

(51) Int. Cl.

| | | |
|---|---|---|
| C07C 5/32 | (2006.01) | |
| F28F 9/02 | (2006.01) | |
| F28F 19/00 | (2006.01) | |
| F28D 7/16 | (2006.01) | |
| F28D 9/00 | (2006.01) | |
| F28F 9/22 | (2006.01) | |
| C10G 35/24 | (2006.01) | |
| C10G 47/36 | (2006.01) | |
| B01J 8/26 | (2006.01) | |
| C10G 11/00 | (2006.01) | |
| G05B 15/02 | (2006.01) | |
| F28D 21/00 | (2006.01) | |

(52) U.S. Cl.
CPC .............. *C07C 5/321* (2013.01); *C10G 11/00* (2013.01); *C10G 35/24* (2013.01); *C10G 47/36* (2013.01); *F28D 7/1607* (2013.01); *F28D 9/0006* (2013.01); *F28D 9/0068* (2013.01); *F28F 9/0239* (2013.01); *F28F 9/22* (2013.01); *F28F 19/00* (2013.01); *F28F 27/00* (2013.01); *G05B 15/02* (2013.01); *B01J 2208/00221* (2013.01); *B01J 2219/00058* (2013.01); *B01J 2219/00065* (2013.01); *B01J 2219/00069* (2013.01); *B01J 2219/00268* (2013.01); *F28D 2021/0022* (2013.01); *F28D 2021/0059* (2013.01); *F28F 9/0278* (2013.01); *F28F 2009/226* (2013.01); *F28F 2200/00* (2013.01); *F28F 2265/00* (2013.01)

(58) Field of Classification Search
CPC .......... B01J 2219/00065; B01J 19/0033; B01J 8/26; B01J 2208/00221; F28F 27/00; F28F 9/0239; F28F 9/22; F28F 19/00; F28F 2265/00; F28F 2200/00; F28F 9/0278; F28F 2009/226; F28D 2021/0022; F28D 7/1607; F28D 9/0006; F28D 9/0068; F28D 2021/0059; C07C 5/321; C07C 11/02; C10G 35/24; C10G 47/36; C10G 11/00
See application file for complete search history.

(56) References Cited

U.S. PATENT DOCUMENTS

| | | | |
|---|---|---|---|
| 4,284,494 A | 8/1981 | Bartholic | 208/164 |
| 4,362,614 A | 12/1982 | Asdigian | 208/235 |
| 4,380,146 A | 4/1983 | Yannone | 60/39.281 |
| 4,385,985 A | 5/1983 | Gross | 208/113 |
| 4,411,773 A | 10/1983 | Gross | 208/159 |
| 4,709,546 A | 12/1987 | Weiler | 415/116 |
| 4,775,460 A | 10/1988 | Reno | |
| 4,795,545 A | 1/1989 | Schmidt | |
| 4,902,469 A | 2/1990 | Watson | 376/216 |
| 5,077,252 A | 12/1991 | Owen et al. | 502/43 |
| 5,227,121 A | 7/1993 | Scarola | 340/525 |
| 5,248,198 A * | 9/1993 | Droege | F28F 19/00 374/43 |
| 5,429,178 A * | 7/1995 | Garey | F28B 11/00 165/11.1 |
| 5,582,684 A | 12/1996 | Holmqvist et al. | 162/49 |
| 5,605,435 A | 2/1997 | Haugen | 137/514 |
| 5,616,214 A | 4/1997 | Leclerc | 162/49 |
| 5,642,296 A | 6/1997 | Saxena | 216/84 |
| 5,666,297 A | 9/1997 | Britt et al. | 364/578 |
| 5,817,517 A | 10/1998 | Perry et al. | 436/55 |
| 6,038,540 A | 3/2000 | Krist et al. | 705/8 |
| 6,081,230 A | 6/2000 | Hoshino | 342/357.32 |
| 6,230,486 B1 | 5/2001 | Yasui | 123/674 |
| 6,266,605 B1 | 7/2001 | Yasui | 60/276 |
| 6,271,845 B1 | 8/2001 | Richardson | 715/764 |
| 6,392,114 B1 | 5/2002 | Shields et al. | 582/719 |
| 6,760,716 B1 | 7/2004 | Ganesamoorthi et al. | 706/21 |
| 6,772,044 B1 | 8/2004 | Mathur et al. | 700/204 |
| 6,795,798 B2 | 9/2004 | Eryurek et al. | 702/188 |
| 6,982,032 B2 | 1/2006 | Shaffer et al. | 210/101 |
| 6,983,227 B1 | 1/2006 | Thalhammer-Reyero | |
| 7,006,889 B2 | 2/2006 | Mathur et al. | 700/204 |
| 7,067,333 B1 | 6/2006 | Pasadyn et al. | 438/5 |
| 7,133,807 B2 | 11/2006 | Karasawa | 702/188 |
| 7,151,966 B1 | 12/2006 | Baier et al. | 700/19 |
| 7,246,039 B2 | 7/2007 | Moorhouse | 702/185 |
| 7,313,447 B2 | 12/2007 | Hsuing et al. | 700/9 |
| 7,415,357 B1 | 8/2008 | Stluka et al. | 702/6 |
| 7,567,887 B2 | 7/2009 | Emigholz et al. | 702/182 |
| 7,742,833 B1 | 6/2010 | Herbst et al. | 700/108 |
| 7,836,941 B2 | 11/2010 | Song et al. | |
| 7,877,596 B2 | 1/2011 | Foo Kune et al. | 713/153 |
| 7,925,979 B2 | 4/2011 | Forney et al. | 715/733 |
| 7,936,878 B2 | 5/2011 | Kune et al. | 380/270 |
| 7,979,192 B2 | 7/2011 | Morrison et al. | |
| 7,995,526 B2 | 8/2011 | Liu et al. | 370/329 |
| 8,050,889 B2 | 11/2011 | Fluegge et al. | 702/182 |
| 8,055,371 B2 | 11/2011 | Sanford et al. | 700/108 |
| 8,111,619 B2 | 2/2012 | Liu et al. | 370/229 |
| 8,128,808 B2 | 3/2012 | Hassan et al. | 208/209 |
| 8,204,717 B2 | 6/2012 | McLaughlin et al. | 702/188 |
| 8,244,384 B2 | 8/2012 | Pachner et al. | 700/30 |
| 8,280,057 B2 | 10/2012 | Budampati et al. | 380/270 |
| 8,347,427 B2 * | 1/2013 | Klicpera | B05B 12/004 4/643 |
| 8,352,049 B2 | 1/2013 | Hsiung et al. | |
| 8,354,081 B2 | 1/2013 | Wheat et al. | |
| 8,385,436 B2 | 2/2013 | Holm et al. | 375/260 |
| 8,428,067 B2 | 4/2013 | Budampati et al. | 370/395.21 |
| 8,458,778 B2 | 6/2013 | Budampati et al. | 726/6 |
| 8,571,064 B2 | 10/2013 | Kore et al. | 370/469 |
| 8,630,962 B2 | 1/2014 | Maeda | 706/12 |
| 8,644,192 B2 | 2/2014 | Budampati et al. | 370/255 |
| 8,811,231 B2 | 8/2014 | Budampati et al. | 370/255 |
| 8,815,152 B2 | 8/2014 | Burgess et al. | |
| 8,923,882 B2 | 12/2014 | Gandhi et al. | 455/455 |
| 8,926,737 B2 | 1/2015 | Chatterjee et al. | |
| 9,053,260 B2 | 6/2015 | Romatier et al. | |
| 9,134,717 B2 | 9/2015 | Trnka | |
| 9,166,667 B2 | 10/2015 | Thanikachalam | |
| 9,176,498 B2 | 11/2015 | Baramov | |
| 9,354,631 B2 | 5/2016 | Mohideen et al. | |
| 9,571,919 B2 | 2/2017 | Zhang et al. | |
| 9,580,341 B1 | 2/2017 | Brown et al. | C02F 3/006 |
| 9,751,817 B2 | 9/2017 | Jani et al. | |
| 9,864,823 B2 | 1/2018 | Horn et al. | |
| 9,968,899 B1 | 5/2018 | Gellaboina et al. | |
| 10,023,341 B1 * | 7/2018 | Christopher | B65B 1/04 |
| 10,095,200 B2 | 10/2018 | Horn et al. | |
| 10,107,295 B1 | 10/2018 | Brecheisen | |
| 10,180,680 B2 | 1/2019 | Horn et al. | |
| 10,183,266 B2 | 1/2019 | Victor et al. | |
| 10,222,787 B2 | 3/2019 | Romatier et al. | |
| 10,328,408 B2 | 6/2019 | Victor et al. | |
| 2002/0123864 A1 | 9/2002 | Eryurek et al. | 702/188 |
| 2002/0179495 A1 | 12/2002 | Heyse et al. | 208/137 |
| 2003/0036052 A1 | 2/2003 | Delwiche et al. | 435/4 |
| 2003/0105775 A1 | 6/2003 | Shimada | |
| 2003/0147351 A1 | 8/2003 | Greenlee | 370/232 |
| 2003/0223918 A1 | 12/2003 | Cammy | 422/144 |
| 2004/0079392 A1 | 4/2004 | Kuechler | 134/22.19 |
| 2004/0099572 A1 | 5/2004 | Evans | 208/113 |
| 2004/0109788 A1 | 6/2004 | Li et al. | 422/3 |
| 2004/0122273 A1 | 6/2004 | Kabin | 585/639 |
| 2004/0122936 A1 | 6/2004 | Mizelle et al. | |
| 2004/0147036 A1 | 7/2004 | Krenn et al. | 436/119 |
| 2004/0148144 A1 | 7/2004 | Martin | |
| 2004/0204775 A1 | 10/2004 | Keyes | 705/30 |
| 2004/0204913 A1 | 10/2004 | Mueller et al. | |
| 2004/0220689 A1 | 11/2004 | Mathur et al. | 700/97 |
| 2004/0220778 A1 | 11/2004 | Imai et al. | 702/188 |
| 2005/0009033 A1 | 1/2005 | Gray et al. | 95/96 |
| 2005/0027721 A1 | 2/2005 | Saenz | 707/100 |
| 2005/0029163 A1 | 2/2005 | Letzsch | 208/113 |

(56) References Cited

U.S. PATENT DOCUMENTS

| | | |
|---|---|---|
| 2005/0133211 A1 | 6/2005 | Osborn et al. |
| 2005/0216209 A1 | 9/2005 | Evans .................. 702/45 |
| 2006/0020423 A1 | 1/2006 | Sharpe, Jr. .............. 702/183 |
| 2006/0133412 A1 | 6/2006 | Callaghan .............. 370/465 |
| 2006/0252642 A1 | 11/2006 | Kanazirev |
| 2006/0259163 A1 | 11/2006 | Hsiung et al. .............. 700/30 |
| 2007/0020154 A1 | 1/2007 | Evans .................. 422/139 |
| 2007/0059159 A1 | 3/2007 | Hjerpe .................. 415/117 |
| 2007/0059838 A1 | 3/2007 | Morrison et al. .............. 436/55 |
| 2007/0091824 A1 | 4/2007 | Budampati et al. .............. 370/255 |
| 2007/0091825 A1 | 4/2007 | Budampati et al. .............. 370/255 |
| 2007/0185664 A1 | 8/2007 | Tanaka .................. 702/56 |
| 2007/0192078 A1 | 8/2007 | Nasle et al. .................. 703/14 |
| 2007/0212790 A1 | 9/2007 | Welch et al. .............. 436/139 |
| 2007/0250292 A1 | 10/2007 | Alagappan et al. .............. 702/184 |
| 2007/0260656 A1 | 11/2007 | Wiig |
| 2007/0271452 A1 | 11/2007 | Foo Kune et al. .............. 713/150 |
| 2008/0086322 A1 | 4/2008 | Wallace .................. 705/1 |
| 2008/0130902 A1 | 6/2008 | Foo Kune et al. .............. 380/286 |
| 2008/0154434 A1 | 6/2008 | Galloway et al. |
| 2008/0217005 A1 | 9/2008 | Stluka et al. .............. 166/250.01 |
| 2008/0282606 A1 | 11/2008 | Plaza et al. |
| 2009/0059786 A1 | 3/2009 | Budampati et al. .............. 370/230 |
| 2009/0060192 A1 | 3/2009 | Budampati et al. .............. 380/270 |
| 2009/0064295 A1 | 3/2009 | Budampati et al. .............. 726/6 |
| 2009/0126899 A1* | 5/2009 | Thybo .................. B60H 1/00978 165/11.1 |
| 2009/0188645 A1* | 7/2009 | Harpster .................. G01K 17/06 165/11.1 |
| 2009/0201899 A1 | 8/2009 | Liu et al. .................. 370/338 |
| 2009/0204245 A1 | 8/2009 | Sustaeta .................. 700/99 |
| 2009/0245286 A1 | 10/2009 | Kore et al. .................. 370/475 |
| 2009/0268674 A1 | 10/2009 | Liu et al. .................. 370/329 |
| 2009/0281677 A1 | 11/2009 | Botich .................. 700/295 |
| 2010/0014599 A1 | 1/2010 | Holm et al. .................. 375/260 |
| 2010/0100404 A1* | 4/2010 | Hodges .................. B01J 19/002 705/7.31 |
| 2010/0108567 A1 | 5/2010 | Medoff .................. 208/49 |
| 2010/0125347 A1 | 5/2010 | Martin et al. .................. 700/31 |
| 2010/0152900 A1 | 6/2010 | Gurciullo et al. |
| 2010/0158764 A1 | 6/2010 | Hedrick .................. 422/134 |
| 2010/0193163 A1* | 8/2010 | Rollins .................. F04D 15/00 165/121 |
| 2010/0230324 A1 | 9/2010 | Al-Alloush et al. .............. 208/82 |
| 2010/0257410 A1* | 10/2010 | Cottrell .................. G05B 23/0229 714/45 |
| 2010/0262900 A1 | 10/2010 | Romatier et al. .............. 715/219 |
| 2011/0108458 A1* | 5/2011 | Leonard .................. C10G 11/18 208/74 |
| 2011/0112659 A1 | 5/2011 | Pachner et al. .................. 700/29 |
| 2011/0152590 A1 | 6/2011 | Sadler et al. .................. 585/313 |
| 2011/0152591 A1 | 6/2011 | Sadler et al. .................. 585/313 |
| 2011/0311014 A1 | 12/2011 | Hottovy et al. .............. 376/283 |
| 2012/0029966 A1 | 2/2012 | Cheewakriengkrai et al. .............. 705/7.25 |
| 2012/0083933 A1 | 4/2012 | Subbu et al. .................. 700/291 |
| 2012/0095808 A1 | 4/2012 | Kattapuram et al. .............. 705/7.37 |
| 2012/0104295 A1 | 5/2012 | Do et al. .................. 251/129.01 |
| 2012/0121376 A1 | 5/2012 | Huis in Het Veld .............. 415/1 |
| 2012/0123583 A1 | 5/2012 | Hazen et al. |
| 2012/0197616 A1 | 8/2012 | Trnka .................. 703/6 |
| 2012/0259583 A1 | 10/2012 | Noboa et al. |
| 2013/0029587 A1 | 1/2013 | Gandhi et al. .................. 455/7 |
| 2013/0031960 A1 | 2/2013 | Delrahim .................. 73/40.5 R |
| 2013/0079899 A1 | 3/2013 | Baramov .................. 700/32 |
| 2013/0090088 A1 | 4/2013 | Chevsky et al. .............. 455/411 |
| 2013/0094422 A1 | 4/2013 | Thanikachalam .............. 370/254 |
| 2013/0172643 A1 | 7/2013 | Pradeep .................. 585/310 |
| 2013/0206359 A1* | 8/2013 | Bertilsson .................. F28F 3/083 165/11.1 |
| 2013/0253898 A1 | 9/2013 | Meagher et al. .............. 703/18 |
| 2013/0270157 A1 | 10/2013 | Ferrara .................. 208/48 AA |
| 2013/0311437 A1 | 11/2013 | Stluka et al. .................. 707/706 |
| 2013/0327052 A1 | 12/2013 | O'Neill .................. 60/772 |
| 2014/0008035 A1 | 1/2014 | Patankar et al. |
| 2014/0026598 A1 | 1/2014 | Trawicki .................. 62/56 |
| 2014/0063565 A1* | 3/2014 | Shan .................. H04N 1/04 358/473 |
| 2014/0074273 A1 | 3/2014 | Mohideen et al. .............. 700/98 |
| 2014/0114039 A1 | 4/2014 | Benham et al. .............. 526/348.5 |
| 2014/0131027 A1 | 5/2014 | Chir .................. 165/300 |
| 2014/0163275 A1 | 6/2014 | Yanagawa et al. .............. 585/319 |
| 2014/0179968 A1 | 6/2014 | Yanagawa et al. .............. 585/476 |
| 2014/0212978 A1 | 7/2014 | Sharpe, Jr. et al. .............. 436/6 |
| 2014/0294683 A1 | 10/2014 | Siedler .................. 422/129 |
| 2014/0294684 A1 | 10/2014 | Siedler .................. 422/129 |
| 2014/0296058 A1 | 10/2014 | Sechrist et al. .................. 502/53 |
| 2014/0309756 A1* | 10/2014 | Trygstad .................. G05B 13/04 700/31 |
| 2014/0337256 A1 | 11/2014 | Varadi et al. .................. 706/12 |
| 2014/0337277 A1 | 11/2014 | Asenjo et al. |
| 2015/0059714 A1 | 3/2015 | Bernards .................. 123/568.11 |
| 2015/0060331 A1 | 3/2015 | Sechrist et al. |
| 2015/0077263 A1 | 3/2015 | Ali et al. .................. 340/679 |
| 2015/0078970 A1 | 3/2015 | Iddir et al. .................. 422/218 |
| 2015/0096736 A1* | 4/2015 | Bronicki .................. F24F 1/48 165/288 |
| 2015/0098862 A1 | 4/2015 | Lok et al. .................. 422/49 |
| 2015/0158789 A1 | 6/2015 | Keusenkothen .............. 60/780 |
| 2015/0176931 A1* | 6/2015 | Aeberhard .................. F24F 11/83 165/200 |
| 2015/0185716 A1 | 7/2015 | Wichmann et al. .............. 700/287 |
| 2015/0276208 A1 | 10/2015 | Maturana et al. .............. 700/274 |
| 2015/0284641 A1 | 10/2015 | Shi .................. 208/113 |
| 2015/0315008 A1* | 11/2015 | Locke .................. B67D 1/0857 222/52 |
| 2015/0330571 A1 | 11/2015 | Beuneken .................. 141/4 |
| 2016/0033941 A1 | 2/2016 | T et al. .................. 700/81 |
| 2016/0048119 A1 | 2/2016 | Wojsznis .................. 700/11 |
| 2016/0069624 A1* | 3/2016 | Rollins .................. F04D 25/028 415/122.1 |
| 2016/0098037 A1 | 4/2016 | Zornio et al. .................. 700/20 |
| 2016/0098234 A1 | 4/2016 | Weaver .................. 358/1.15 |
| 2016/0122663 A1 | 5/2016 | Pintart et al. |
| 2016/0147204 A1 | 5/2016 | Wichmann et al. .............. 700/287 |
| 2016/0237910 A1 | 8/2016 | Saito |
| 2016/0238288 A1* | 8/2016 | Zoetemeijer .............. G01K 11/32 |
| 2016/0260041 A1 | 9/2016 | Horn et al. |
| 2016/0291584 A1 | 10/2016 | Horn et al. |
| 2016/0292188 A1 | 10/2016 | Horn et al. |
| 2016/0292325 A1 | 10/2016 | Horn et al. |
| 2016/0313653 A1 | 10/2016 | Mink |
| 2016/0320291 A1* | 11/2016 | Najjar .................. G01N 17/008 |
| 2016/0363315 A1 | 12/2016 | Colannino et al. |
| 2017/0009932 A1 | 1/2017 | Oh |
| 2017/0058213 A1 | 3/2017 | Oprins .................. 585/303 |
| 2017/0082320 A1 | 3/2017 | Wang |
| 2017/0107188 A1 | 4/2017 | Kawaguchi |
| 2017/0211900 A1* | 7/2017 | Kubo .................. F28F 27/00 |
| 2017/0276571 A1* | 9/2017 | Vitullo .................. G05B 23/0248 |
| 2017/0284410 A1 | 10/2017 | Sharpe, Jr. |
| 2017/0315543 A1 | 11/2017 | Horn et al. |
| 2017/0323038 A1 | 11/2017 | Horn et al. |
| 2017/0352899 A1 | 12/2017 | Asai |
| 2017/0370660 A1* | 12/2017 | Alahyari .................. F28B 9/08 |
| 2018/0046155 A1 | 2/2018 | Horn et al. |
| 2018/0081344 A1 | 3/2018 | Romatier et al. |
| 2018/0082569 A1 | 3/2018 | Horn et al. |
| 2018/0113442 A1* | 4/2018 | Nixon .................. G05B 19/4184 |
| 2018/0121581 A1 | 5/2018 | Horn et al. |
| 2018/0122021 A1 | 5/2018 | Horn et al. |
| 2018/0155638 A1 | 6/2018 | Al-Ghamdi .................. 208/79 |
| 2018/0155642 A1 | 6/2018 | Al-Ghamdi et al. |
| 2018/0197350 A1 | 7/2018 | Kim |
| 2018/0275690 A1 | 9/2018 | Lattanzio et al. |
| 2018/0275691 A1 | 9/2018 | Lattanzio et al. |
| 2018/0275692 A1 | 9/2018 | Lattanzio et al. |
| 2018/0280914 A1 | 10/2018 | Victor et al. |
| 2018/0280917 A1 | 10/2018 | Victor et al. |
| 2018/0282633 A1 | 10/2018 | Van de Cotte et al. |
| 2018/0282634 A1 | 10/2018 | Van de Cotte et al. |
| 2018/0282635 A1 | 10/2018 | Van de Cotte et al. |
| 2018/0283368 A1 | 10/2018 | Van de Cotte et al. |

(56) References Cited

U.S. PATENT DOCUMENTS

| | | |
|---|---|---|
| 2018/0283392 A1 | 10/2018 | Van de Cotte et al. |
| 2018/0283404 A1* | 10/2018 | Van de Cotte ........ F04D 29/701 |
| 2018/0283811 A1 | 10/2018 | Victor et al. |
| 2018/0283812 A1 | 10/2018 | Victor et al. |
| 2018/0283813 A1 | 10/2018 | Victor et al. |
| 2018/0283815 A1 | 10/2018 | Victor et al. |
| 2018/0283816 A1 | 10/2018 | Victor et al. |
| 2018/0283818 A1 | 10/2018 | Victor et al. |
| 2018/0284705 A1 | 10/2018 | Van de Cotte et al. |
| 2018/0286141 A1 | 10/2018 | Van de Cotte et al. |
| 2018/0311609 A1 | 11/2018 | McCool et al. |
| 2018/0362862 A1 | 12/2018 | Gellaboina et al. |
| 2018/0363914 A1 | 12/2018 | Faiella et al. |
| 2018/0364747 A1 | 12/2018 | Charr et al. |
| 2019/0002318 A1 | 1/2019 | Thakkar et al. |
| 2019/0003978 A1 | 1/2019 | Shi et al. |
| 2019/0015806 A1 | 1/2019 | Gellaboina et al. |
| 2019/0041813 A1 | 2/2019 | Horn et al. |
| 2019/0083920 A1 | 3/2019 | Bjorklund et al. |
| 2019/0101336 A1 | 4/2019 | Victor et al. |
| 2019/0101342 A1 | 4/2019 | Victor et al. |
| 2019/0101907 A1 | 4/2019 | Charr et al. |
| 2019/0102966 A1 | 4/2019 | Lorenz |
| 2019/0108454 A1 | 4/2019 | Banerjee et al. |
| 2019/0120810 A1 | 4/2019 | Kumar KN et al. |
| 2019/0151814 A1 | 5/2019 | Victor et al. |
| 2019/0155259 A1 | 5/2019 | Romatier et al. |
| 2019/0227504 A1* | 7/2019 | Ma ........................ G05B 13/042 |

FOREIGN PATENT DOCUMENTS

| | | | | |
|---|---|---|---|---|
| EP | 2801937 A1 | 11/2014 | ............. | G06Q 10/06 |
| GB | 1134439 A | 11/1968 | ............. | G01N 31/22 |
| WO | WO 1990/010083 A1 | 9/1990 | ............... | C12Q 1/04 |
| WO | WO 2001/060951 A1 | 8/2001 | ............. | C10G 51/04 |
| WO | WO 2006/044408 A1 | 4/2006 | ............. | F23D 14/72 |
| WO | WO 2007/095585 A2 | 8/2007 | ........... | A61K 31/721 |
| WO | WO 2009/046095 A1 | 4/2009 | ............. | G06F 11/00 |
| WO | WO 2014/042508 A1 | 3/2014 | ............. | G06Q 50/04 |
| WO | WO 2014/123993 A1 | 8/2014 | ............. | G06F 17/00 |
| WO | WO 2016/141128 A1 | 9/2016 | ............. | G06Q 10/06 |
| WO | WO 2017/079058 A1 | 5/2017 | ............... | B01D 1/14 |

OTHER PUBLICATIONS

Nawaz, "Light alkane dehydrogenation to light olefin technologies: a comprehensive review", 2015, pp. 1-24, downloaded from the internet https://www.researchgate.net/profile/Dr_Zeeshan_Nawaz/publication/282464043_Light . . . (Year: 2015).*
Hale, "Understanding and preventing heat exchanger fouling", Nov. 2019, p. 9 downloaded from the internet https://www.watertechonline.com/process-water/article/14071807/understanding-and-preventing-heat-exchanger-fouling (Year: 2019).*
Mostafa M. Awad, "Fouling of Heat Transfer Surfaces", Heat Transfer—Theoretical Analysis, Experimental Investigations and Industrial Systems, ISBN: 978-953-307-226-5, InTech, 2011, p. 41, Available from: http://www.intechopen.com/books/heat-transfer-theoretical-analysis-experimental-investigation (Year: 2011).*
Daniel Goebel, Dry Gas Seal Contamination During Operation and Pressurization Hold, [online], Feb. 2016, [retrieved on Jun. 19, 2019]. Retrieved from <https ://core.ac.uk/download/pdf/84815277. pdf> (Year: 2016), pp. 1-12.
EnergyMEDOR®, Product brochure (Nov. 2014), pp. 2.
Chistof Huber, Density and Concentration Measurement Application for Novel MEMS-based Micro Densitometer for Gas, [online], 2016, [retrieved on Jun. 19, 2019]. Retrieved from <https://www.ama-science.org/proceedings/getFile/ZwZ1 BD==> (Year: 2016), pp. 263-267.
Lotters, Real-time Composition Determination of Gas Mixtures, [online], 2015, [retrieved on Jun. 19, 2019]. Retrieved from <https://www.ama-science.org/proceedings/getFile/ZwNOZj==>(Year: 2015), pp. 712-717.
Maybeck, Peter S., "Stochastic models, estimation, and control," vol. 1, Academic Press (1979), 19 pages.
U.S. Appl. No. 15/058,658, filed Mar. 3, 2015, Ian G. Horn Zak Alzein Paul Kowalczyk Christophe Romatier, System And Method For Managing Web-Based Refinery Performance Optimization Using Secure Cloud Computing.
U.S. Appl. No. 15/640,120, filed Mar. 30, 2015, Ian G. Horn Zak Alzein Paul Kowalczyk Christophe Romatier, Evaluating Petrochemical Plant Errors To Determine Equipment Changes For Optimized Operations.
U.S. Appl. No. 15/851,207, filed Mar. 27, 2017, Louis A. Lattanzio Alex Green Ian G. Horn Matthew R. Wojtowicz, Operating Slide Valves In Petrochemical Plants Or Refineries.
U.S. Appl. No. 15/851,343, filed Dec. 21, 2017, Louis A. Lattanzio Alex Green Ian G. Horn Matthew R. Wojtowicz, Early Prediction And Detection Of Slide Valve Sticking In Petrochemical Plants Or Refineries.
U.S. Appl. No. 15/851,360, filed Mar. 27, 2011, Louis A. Lattanzio Alex Green Ian G. Horn Matthew R. Wojtowicz, Measuring And Determining Hot Spots In Slide Valves For Petrochemical Plants Or Refineries.
U.S. Appl. No. 15/853,689, filed Mar. 30, 2015, Ian G. Horn Zak Alzein Paul Kowalczyk Christophe Romatier, Cleansing System For A Feed Composition Based On Environmental Factors.
U.S. Appl. No. 15/858,767, filed Dec. 28, 2017, Ian G. Horn Zak Alzein Paul Kowalczyk Christophe Romatier, Chemical Refinery Performance Optimization.
U.S. Appl. No. 15/899,967, filed Feb. 20, 2018, Joel Kaye, Developing Linear Process Models Using Reactor Kinetic Equations.
U.S. Appl. No. 15/935,827, filed Mar. 28, 2017, Michael R. Van de Cotte Ian G. Horn, Rotating Equipment In A Petrochemical Plant Or Refinery.
U.S. Appl. No. 15/935,847, filed Mar. 28, 2017, Michael R. Van de Cotte Ian G. Horn, Rotating Equipment In A Petrochemical Plant Or Refinery.
U.S. Appl. No. 15/935,872, filed Mar. 28, 2017, Michael R. Van de Cotte Ian G. Horn, Early Surge Detection Of Rotating Equipment In A Petrochemical Plant Or Refinery.
U.S. Appl. No. 15/935,898, filed Mar. 28, 2017, Michael R. Van de Cotte Ian G. Horn, Reactor Loop Fouling Monitor For Rotating Equipment In A Petrochemical Plant Or Refinery.
U.S. Appl. No. 15/935,920, filed Mar. 28, 2017, Michael R. Van de Cotte Ian G. Horn, Sensor Location For Rotating Equipment In A Petrochemical Plant Or Refinery.
U.S. Appl. No. 15/935,935, filed Mar. 28, 2017, Michael R. Van de Cotte Ian G. Horn, Determining Quality Of Gas For Rotating Equipment In A Petrochemical Plant Or Refinery.
U.S. Appl. No. 15/935,950, filed Mar. 28, 2017, Michael R. Van de Cotte Ian G. Horn, Determining Quality Of Gas For Rotating Equipment In A Petrochemical Plant Or Refinery.
U.S. Appl. No. 15/935,957, filed Mar. 28, 2017, Michael R. Van de Cotte Ian G. Horn, Using Molecular Weight And Invariant Mapping To Determine Performance Of Rotating Equipment In A Petrochemical Plant Or Refinery.
U.S. Appl. No. 15/937,484, filed Mar. 28, 2017, Sanford A. Victor Phillip F. Daly Ian G. Horn, Detecting And Correcting Maldistribution In Heat Exchangers In A Petrochemical Plant Or Refinery.
U.S. Appl. No. 15/937,499, filed Mar. 28, 2017, Sanford A. Victor Phillip F. Daly Ian G. Horn, Detecting And Correcting Cross-Leakage In Heat Exchangers In A Petrochemical Plant Or Refinery.
U.S. Appl. No. 15/937,517, filed Mar. 28, 2017, Sanford A. Victor Phillip F. Daly Ian G. Horn, Strain Gauges And Detecting Pre-Leakage In Heat Exchangers In A Petrochemical Plain Or Refinery.
U.S. Appl. No. 15/937,535, filed Mar. 28, 2017, Sanford A. Victor Phillip F. Daly Ian G. Horn, Detecting And Correcting Thermal Stresses In Heat Exchangers In A Petrochemical Plant Or Refinery.
U.S. Appl. No. 15/937,588, filed Mar. 28, 2017, Sanford A. Victor Phillip F. Daly Ian G. Horn, Detecting And Correcting Problems In Liquid Lifting In Heat Exchangers.
U.S. Appl. No. 15/937,602, filed Mar. 28, 2017, Sanford A. Victor Phillip F. Daly Ian G. Horn, Air-Cooled Heat Exchangers.
U.S. Appl. No. 15/937,614, filed Mar. 28, 2017, Sanford A. Victor Phillip F. Daly Ian G. Horn, Wet-Cooled Heat Exchanger.

(56) References Cited

OTHER PUBLICATIONS

U.S. Appl. No. 15/937,624, filed Mar. 28, 2017, Sanford A. Victor Phillip F. Daly Ian G. Horn, Heat Exchangers In A Petrochemical Plant Or Refinery.
U.S. Appl. No. 15/963,840, filed Apr. 28, 2017, Ryan McCool Chad E. Bjorklund Jorge Charr Luk Verhulst, Remote Monitoring Of Adsorber Process Units.
U.S. Appl. No. 15/972,974, filed Jun. 20, 2017, Jorge Charr Kevin Carnes Ralph Davis Donald A. Eizenga Christina L. Haasser James W. Harris Raul A. Ohaco Daliah Papoutsis, Incipient Temperature Excursion Mitigation And Control.
U.S. Appl. No. 15/979,421, filed May 14, 2018, Mahesh K. Gellaboina Louis A. Lattanzio, Catalyst Transfer Pipe Plug Detection.
U.S. Appl. No. 16/007,669, filed Jun. 28, 2017, Yili Shi Daliah Papoutsis Jonathan Andrew Tertel, Process And Apparatus To Detect Mercaptans In A Caustic Stream.
U.S. Appl. No. 16/011,600, filed Jun. 19, 2017, Theodore Peter Faiella Colin J. Deller Raul A. Ohaco, Remote Monitoring Of Fired Heaters.
U.S. Appl. No. 16/011,614, filed Jun. 19, 2017, Mahesh K, Gellaboina Michael Terry Seth Huber Danielle Schindlbeck, Catalyst Cycle Length Prediction Using Eigen Analysis.
U.S. Appl. No. 16/015,579, filed Jun. 28, 2017, Killol H. Thakkar Robert W. Brafford Eric C. Tompkins, Process And Apparatus For Dosing Nutrients To A Bioreactor.
U.S. Appl. No. 16/133,623, filed Sep. 18, 2017, Chad E. Bjorklund Jeffrey Guenther Stephen Kelley Ryan McCool, Remote Monitoring Of Pressure Swing Adsoiption Units.
U.S. Appl. No. 16/140,770, filed Oct. 20, 2017, Dinesh Kumar KN Soumendra Mohan Banerjee, System And Method To Optimize Crude Oil Distillation Or Other Processing By Inline Analysis Of Crude Oil Properties.
U.S. Appl. No. 16/148,763, filed Oct. 2, 2017, Jorge Charr Bryan J. Egolf Dean E. Rende Mary Wier Guy B. Woodle Carol Zhu, Remote Monitoring Of Chloride Treaters Using A Process Simulator Based Chloride Distribution Estimate.
U.S. Appl. No. 16/151,086, filed Oct. 5, 2017, Soumendra Mohan Banerjee Deepak Bisht Priyesh Jayendrakumar Jani Krishna Mani Gautam Pandey, Harnessing Machine Learning & Data Analytics For A Real Time Predictive Model For A Fcc Pre-Treatment Unit.
U.S. Appl. No. 16/154,138, filed Oct. 8, 2018, Raul A. Ohaco Jorge Charr, High Purity Distillation Process Control With Multivatiable And Model Predictive Control (Mpc) And Fast Response Analyzer.
U.S. Appl. No. 16/154,141, filed Oct. 8, 2018, Ian G. Horn Zak Alzein Paul Kowalczyk Christophe Romatier, System And Method For Improving Performance Of A Plant With A Furnace.
U.S. Appl. No. 16/215,101, filed Dec. 10, 2018, Louis A. Lattanzio Christopher Schindlbeck, Delta Temperature Control Of Catalytic Dehydrogenation Process Reactors.
U.S. Appl. No. 16/252,021, filed Sep. 16, 2016, Christophe Romatier Zak Alzein Ian G. Horn Paul Kowalczyk David Rondeau, Petrochemical Plant Diagnostic System And Method For Chemical Process Model Analysis.
U.S. Appl. No. 16/253,181, filed Mar. 28, 2017, Ian G. Horn Phillip F. Daly Sanford A. Victor, Detecting And Correcting Vibration In Heat Exchangers.
U.S. Appl. No. 16/363,406, filed Mar. 30, 2018, Louis A. Lattanzio Abhishek Pecthekar, Catalytic Dehydrogenation Reactor Performance Index.
Jul. 12, 2018—(WO) International Search Report—App PCT/US2018/024894, pp. 7.
Sep. 20, 2018—U.S. Notice of Allowance—U.S. Appl. No. 15/937,579, pp. 10.

\* cited by examiner

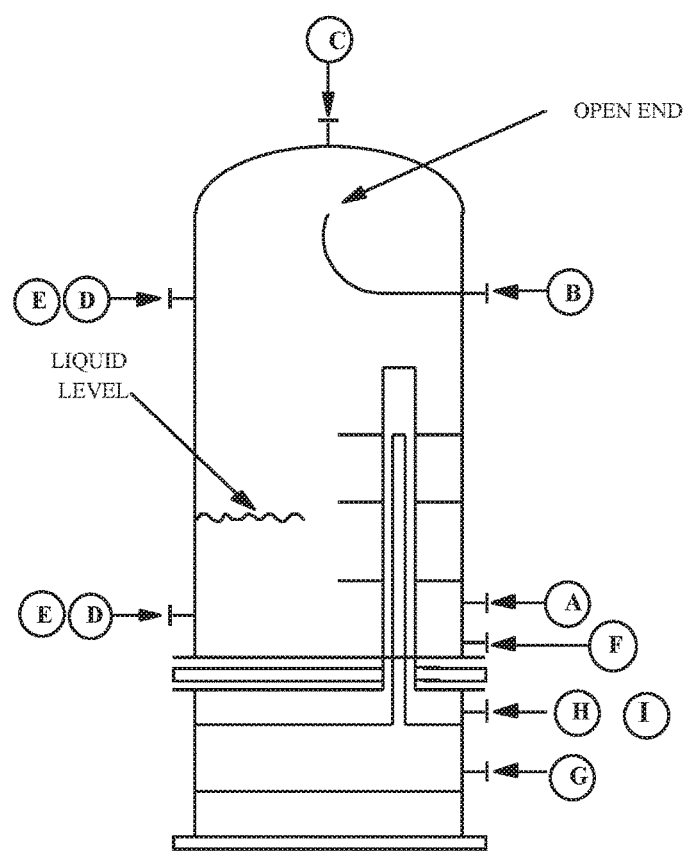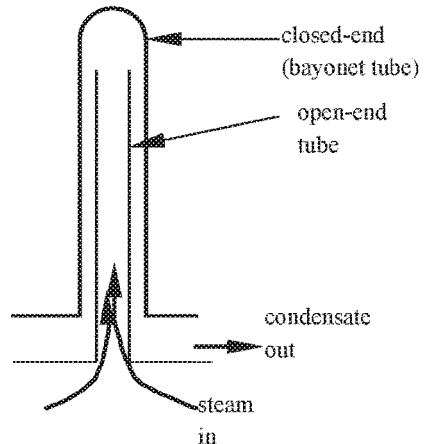
FIG. 5A
FIG. 5B

AIR-COOLED HEAT EXCHANGERS

CROSS-REFERENCE TO RELATED APPLICATION

This application claims the benefit of priority under 35 U.S.C. § 119(e) of U.S. Provisional Application No. 62/477,729, filed Mar. 28, 2017, which is incorporated by reference in its entirety.

FIELD

The present disclosure is related to a method and system for managing the operation of a plant, such as a chemical plant or a petrochemical plant or a refinery, and more particularly to a method for improving the performance of components that make up operations in a plant. Typical plants may be those that provide catalytic dehydrogenation or hydrocarbon cracking, or catalytic reforming, or other process units.

BACKGROUND

A plant or refinery may include one or more pieces of equipment for performing a process. Equipment may break down over time, and need to be repaired or replaced. Additionally, a process may be more or less efficient depending on one or more operating characteristics. There will always be a need for improving process efficiencies and improving equipment reliability.

SUMMARY

The following summary presents a simplified summary of certain features. The summary is not an extensive overview and is not intended to identify key or critical elements.

One or more embodiments may include a system that includes a reactor; a heater; an air-cooled heat exchanger; a regenerator; a separator; one or more sensors associated with the air-cooled heat exchanger; a data collection platform; and/or a data analysis platform. The data collection platform may include one or more processors of the data collection platform; a communication interface of the data collection platform; and memory storing executable instructions that, when executed, cause the data collection platform to: receive, from the one or more sensors associated with the air-cooled heat exchanger, sensor data comprising operation information associated with the air-cooled heat exchanger; correlate the sensor data from the one or more sensors with metadata comprising time data, the time data corresponding to the operation information associated with the air-cooled heat exchanger; and transmit the sensor data. The data analysis platform may include one or more processors of the data analysis platform; a communication interface of the data analysis platform; and memory storing executable instructions that, when executed, cause the data analysis platform to: receive, from the data collection platform, the sensor data comprising the operation information associated with the air-cooled heat exchanger; analyze the sensor data comprising the operation information associated with the air-cooled heat exchanger; based on analyzing the sensor data comprising the operation information associated with the air-cooled heat exchanger, determine a problem in an operating condition of the air-cooled heat exchanger; based on the problem in the operating condition of the air-cooled heat exchanger, determine a recommended adjustment to the operating condition of the air-cooled heat exchanger; and send a command configured to cause the recommended adjustment to the operating condition of the air-cooled heat exchanger.

One or more embodiments may include one or more non-transitory computer-readable media storing executable instructions that, when executed, cause a system to: receive sensor data comprising operation information associated with a heat exchanger; analyze the sensor data comprising the operation information associated with the air-cooled heat exchanger; based on analyzing the sensor data comprising the operation information associated with the air-cooled heat exchanger, determine a problem in an operating condition of the air-cooled heat exchanger; based on the problem in the operating condition of the air-cooled heat exchanger, determine a recommended adjustment to the operating condition of the air-cooled heat exchanger; and send a command configured to cause the recommended adjustment to the operating condition of the air-cooled heat exchanger.

One or more embodiments may include a method that includes receiving, by a data analysis computing device, sensor data comprising operation information associated with a heat exchanger; analyzing, by the data analysis computing device, the sensor data comprising the operation information associated with the air-cooled heat exchanger; based on analyzing the sensor data comprising the operation information associated with the air-cooled heat exchanger, determining, by the data analysis computing device, a problem in an operating condition of the air-cooled heat exchanger; based on the problem in the operating condition of the air-cooled heat exchanger, determining, by the data analysis computing device, a recommended adjustment to the operating condition of the air-cooled heat exchanger; and sending, by the data analysis computing device, a command configured to cause the recommended adjustment to the operating condition of the air-cooled heat exchanger.

Other technical features may be readily apparent to one skilled in the art from the following figures, descriptions, and claims.

BRIEF DESCRIPTION OF DRAWINGS

The present disclosure is illustrated by way of example and not limited in the accompanying figures in which like reference numerals indicate similar elements and in which:

FIGS. 5A and 5B depict vaporizers in accordance with one or more example embodiments;

DETAILED DESCRIPTION

In the following description of various illustrative embodiments, reference is made to the accompanying drawings, which form a part hereof, and in which is shown, by way of illustration, various embodiments in which aspects of the disclosure may be practiced. It is to be understood that other embodiments may be utilized, and structural and functional modifications may be made, without departing from the scope of the present disclosure.

It is noted that various connections between elements are discussed in the following description. It is noted that these connections are general and, unless specified otherwise, may be direct or indirect, wired or wireless, and that the specification is not intended to be limiting in this respect.

A chemical plant or a petrochemical plant or a refinery may include one or more pieces of equipment that process one or more input chemicals to create one or more products. For example, catalytic dehydrogenation can be used to convert paraffins to the corresponding olefin, e.g., propane to propene, or butane to butene.

A multitude of process equipment may be utilized in the chemical, refining, and petrochemical industry including, but not limited to, slide valves, rotating equipment, pumps, compressors, heat exchangers, fired heaters, control valves, fractionation columns, reactors, and/or shut-off valves.

Elements of chemical and petrochemical/refinery plants may be exposed to the outside and thus can be exposed to various environmental stresses. Such stresses may be weather related, such as temperature extremes (hot and cold), high-wind conditions, and precipitation conditions such as snow, ice, and rain. Other environmental conditions may be pollution particulates, such as dust and pollen, or salt if located near an ocean, for example. Such stresses can affect the performance and lifetime of equipment in the plants. Different locations may have different environmental stresses. For example, a refinery in Texas may have different stresses than a chemical plant in Montana.

Process equipment may deteriorate over time, affecting the performance and integrity of the process. Such deteriorating equipment may ultimately fail, but before failing, may decrease efficiency, yield, and/or product properties.

Figure 1:
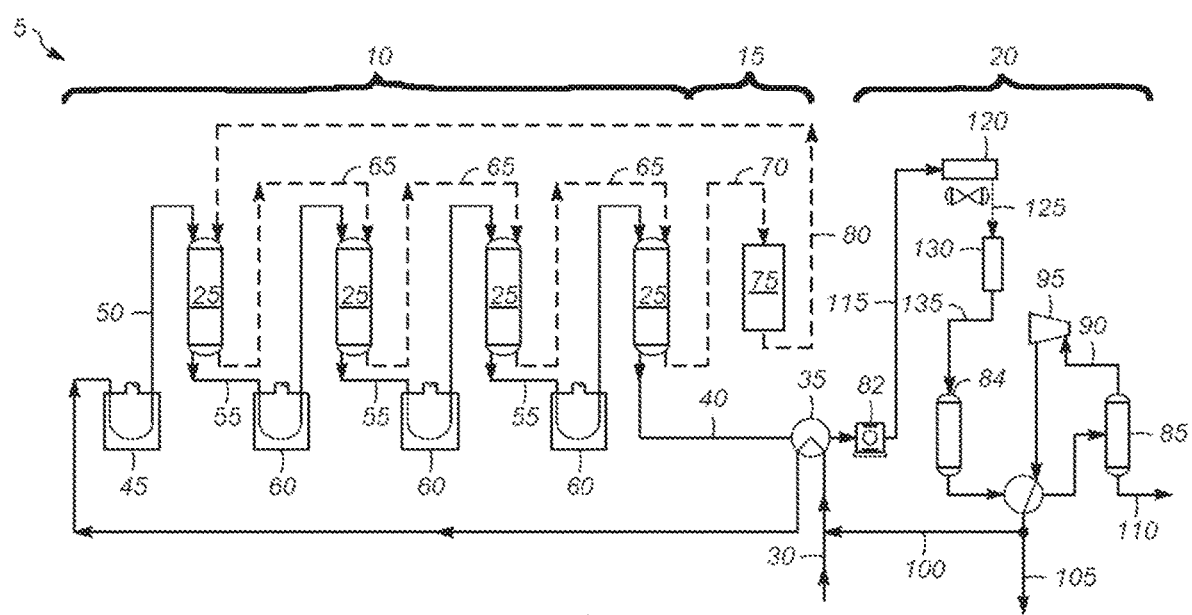
FIG. 1 depicts an illustrative arrangement for a catalytic dehydrogenation process in accordance with one or more example embodiments.

FIG. 1 shows one typical arrangement for a catalytic dehydrogenation process 5. The process 5 includes a reactor section 10, a catalyst regeneration section 15, and a product recovery section 20.

The reactor section 10 includes one or more reactors 25. A hydrocarbon feed 30 is sent to a heat exchanger 35 where it exchanges heat with a reactor effluent 40 to raise the feed temperature. The feed 30 is sent to a preheater 45 where it is heated to the desired inlet temperature. The preheated feed 50 is sent from the preheater 45 to the first reactor 25. Because the dehydrogenation reaction is endothermic, the temperature of the effluent 55 from the first reactor 25 is less than the temperature of the preheated feed 50. The effluent 55 is sent to interstage heaters 60 to raise the temperature to the desired inlet temperature for the next reactor 25.

After the last reactor, the reactor effluent 40 is sent to the heat exchanger 35, and heat is exchanged with the feed 30. The reactor effluent 40 is then sent to the product recovery section 20. The catalyst 65 moves through the series of reactors 25. When the catalyst 70 leaves the last reactor 25, it is sent to the catalyst regeneration section 15. The catalyst regeneration section 15 includes a regenerator 75 where coke on the catalyst is burned off and the catalyst may go through a reconditioning step. A regenerated catalyst 80 is sent back to the first reactor 25.

The reactor effluent 40 is compressed in the compressor or centrifugal compressor 82. The compressed effluent 115 is introduced to a cooler 120, for instance a heat exchanger. The cooler 120 lowers the temperature of the compressed effluent. The cooled effluent 125 (cooled product stream) is then introduced into a chloride remover 130, such as a chloride scavenging guard bed. The chloride remover 130 includes an adsorbent, which adsorbs chlorides from the cooled effluent 125 and provides a treated effluent 135. Treated effluent 135 is introduced to a drier 84.

The dried effluent is separated in separator 85. Gas 90 is expanded in expander 95 and separated into a recycle hydrogen stream 100 and a net separator gas stream 105. A liquid stream 110, which includes the olefin product and unconverted paraffin, is sent for further processing, where the desired olefin product is recovered and the unconverted paraffin is recycled to the dehydrogenation reactor 25.

Also known is a fluid catalytic cracking (FCC) process which includes an FCC fluidized bed reactor and a spent catalyst regenerator. Regenerated cracking catalyst entering the reactor, from the spent catalyst regenerator, is contacted with an FCC feed stream in a riser section at the bottom of the FCC reactor, to catalytically crack the FCC feed stream and provide a product gas stream, comprising cracked hydrocarbons having a reduced molecular weight, on average, relative to the average molecular weight of feed hydrocarbons in the FCC feed stream. Steam and lift gas are used as carrier gases that upwardly entrain the regenerated catalyst in the riser section, as it contacts the FCC feed. In this riser section, heat from the catalyst vaporizes the FCC feed stream, and contact between the catalyst and the FCC feed causes cracking of this feed to lower molecular weight hydrocarbons, as both the catalyst and feed are transferred up the riser and into the reactor vessel. A product gas stream comprising the cracked (e.g., lower molecular weight) hydrocarbons is separated from spent cracking catalyst at or near the top of the reactor vessel, preferably using internal solid/vapor separation equipment, such as cyclone separators. This product gas stream, essentially free of spent cracking catalyst, then exits the reactor vessel through a product outlet line for further transport to the downstream product recovery section.

The spent or coked catalyst, following its disengagement or separation from the product gas stream, requires regeneration for further use. This coked catalyst first falls into a dense bed stripping section of the FCC reactor, into which steam is injected, through a nozzle and distributor, to purge any residual hydrocarbon vapors that would be detrimental to the operation of the regenerator. After this purging or stripping operation, the coked catalyst is fed by gravity to the catalyst regenerator through a spent catalyst standpipe. A regenerator can also be referred to as a combustor. Regenerators may have various configurations. In the spent catalyst regenerator, a stream of oxygen-containing gas, such as air, is introduced to contact the coked catalyst, burn coke deposited thereon, and provide regenerated catalyst, having most or all of its initial coke content converted to combustion products, including $CO_2$, CO, and $H_2O$ vapors that exit in a flue gas stream. The regenerator operates with catalyst and the oxygen-containing gas (e.g., air) flowing upwardly together in a combustor riser that is located within the catalyst regenerator. At or near the top of the regenerator, following combustion of the catalyst coke, regenerated cracking catalyst is separated from the flue gas using internal solid/vapor separation equipment (e.g., cyclones) to promote efficient disengagement between the solid and vapor phases.

In the FCC recovery section, the product gas stream exiting the FCC reactor is fed to a bottoms section of an FCC main fractionation column. Several product fractions may be separated on the basis of their relative volatilities and recovered from this main fractionation column. Representative product fractions include, for example, naphtha (or FCC gasoline), light cycle oil, and heavy cycle oil.

Other petrochemical processes produce desirable products, such as turbine fuel, diesel fuel and other products referred to as middle distillates, as well as lower boiling hydrocarbon liquids, such as naphtha and gasoline, by hydrocracking a hydrocarbon feedstock derived from crude oil or heavy fractions thereof. Feedstocks most often subjected to hydrocracking are the gas oils and heavy gas oils recovered from crude oil by distillation.

References herein to a "plant" are to be understood to refer to any of various types of chemical and petrochemical manufacturing or refining facilities. References herein to a plant "operators" are to be understood to refer to and/or include, without limitation, plant planners, managers, engineers, technicians, and others interested in, overseeing, and/or running the daily operations at a plant.

Heat Exchangers

Heat Exchangers have many purposes in chemical and petrochemical plants. There are many different types of heat exchangers with the selection based on the specifics of its intended purpose. A typical use is to increase the temperature of the feed stream and reduce the temperature of a product stream or intermediate stream. For example, for a combined feed-effluent exchanger (CFE), an upstream process unit, or a fractionation column, or a pump may be directly upstream for the cold feed inlet; a recycle gas compressor is upstream of the cold recycle gas inlet; a fired heater is downstream of the cold outlet; a reactor is upstream of the hot effluent inlet; a product condenser (air-cooled, water-cooled, or both) is downstream of the hot effluent outlet.

Heat exchangers may be classified by their flow arrangement. Flow schemes reference how the hot stream and the cold stream are arranged (and therefore affect the temperature difference driving force for heat transfer between the two streams), and can refer to either overall flow through the exchanger (nozzle to nozzle) or locally (within a baffle cross-pass or a plate pass).

Parallel flow refers to two flows traveling in the same direction. Counter flow refers to two flows traveling in opposite directions. Cross flow refers to two (typically locally) flows that are perpendicular to each other.

Types of heat exchangers include, but are not limited to, shell and tube heat exchangers, plate heat exchangers, plate and shell heat exchangers, plate fin heat exchangers, and/or air cooled heat exchangers. Metal plates form the bundle and channels between the plates form the passages for flow. Other heat exchangers may be air-cooled heat exchangers and wetted surface air coolers. The heat exchangers may be vertically oriented or horizontally oriented.

Particular types of heat exchangers include combined feed exchangers (horizontal shells in series), column reboiler, column condenser, column trim condenser, column feed-bottoms exchanger, column bottoms cooler, feed heater, effluent cooler, chiller, cooler, heater, and vaporizer. Air exchangers typically use ambient air to cool streams of gas or liquid. A cold box combines brazed heat exchangers with any type of complementary cryogenic equipment, such as knock-out drums, two-phase injection drums, distillation columns, interconnecting piping, valves and instrumentation, for example used to separate product streams at cold temperatures.

In some aspects, a cold stream, which is a mixture of feed and recycle gas, needs to be heated and a hot stream, which is reactor effluent, needs to be cooled. The recycle gas is typically hydrogen-rich recycle gas. The feed may be liquid feed or gas feed which is mixed then with the recycle gas. If a liquid feed the combined feed and recycle gas forms a two phase system. The temperatures of the feed/recycle gas and effluent entering the exchanger depend on the particular process.

Vertically oriented heat exchangers can be used in many processes, including hydrocarbon processes. Often, a vertically oriented exchanger may be used to preheat a mixed phase of a liquid hydrocarbon feed and a gas rich in hydrogen. Typically, a vertically oriented exchanger is used as a combined feed and effluent (hereinafter may be abbreviated "CFE") exchanger where a mixed phase of a hydrocarbon liquid and a gas are preheated with the effluent from a reactor. Often, a liquid hydrocarbon feed and a gas, often a recycle gas including hydrogen, are mixed and introduced on the tube side. Generally, the mixture requires good lift to pass upwards through the vertically oriented heat exchanger.

Figure 2:
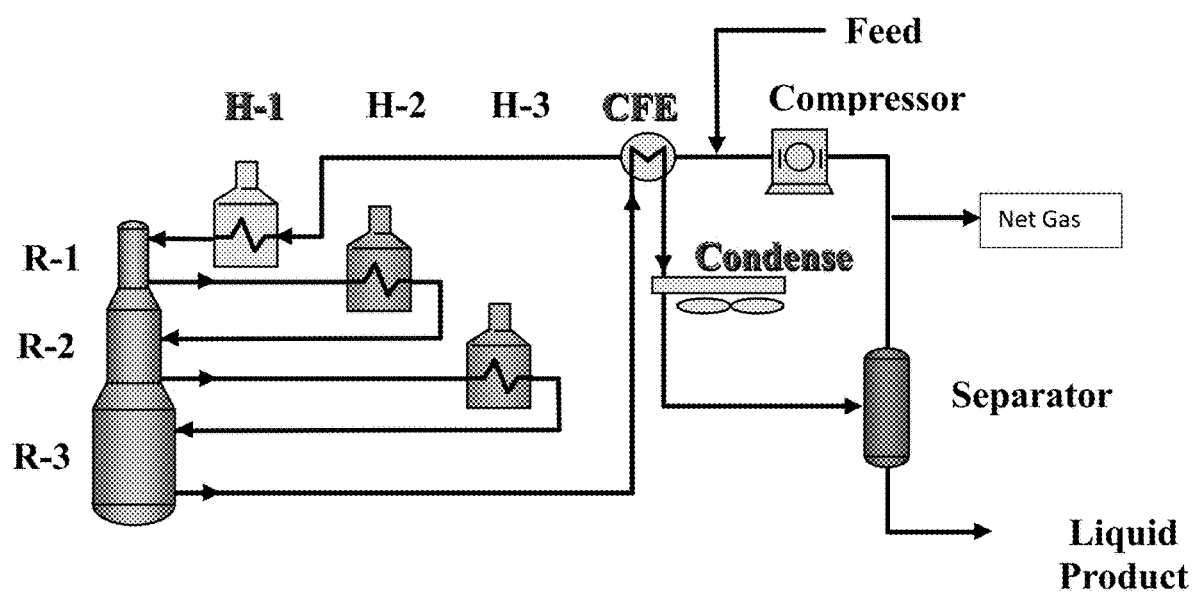
FIG. 2 depicts an illustrative catalytic reforming process using a (vertically-oriented) combined feed-effluent (CFE) exchanger in accordance with one or more example embodiments.

FIG. 2 illustrates a process for reforming with continuous catalyst regeneration (CCR) using a (vertically oriented) combined feed-effluent (CFE) exchanger. The cold stream, a combination of liquid feed (110.4° C.) with hydrogen rich recycle gas (e.g., light paraffins) (125.8° C.), is introduced into a CFE exchanger where the feed is vaporized. (Entrance temperature: 96.9° C. Exit temperature: 499.6° C.) The feed/recycle exits the CFE as a gas and goes through a series of heating and reaction steps. The resulting product effluent or hot stream is introduced into the CFE exchanger and is cooled down. (Entrance temperature: 527.9° C. Exit temperature: 109.1° C.) The effluent exits the CFE exchanger and is then cooled down further and condensed using an air cooler. The liquid product is separated from the gas stream containing hydrogen and light paraffins. Some of the gas stream is removed, for example as a product, and the rest of the stream is used as recycle gas.

A catalytic dehydrogenation process (e.g., an OLEFLEX process) with continuous catalyst regeneration (CCR) may use a (vertically-oriented) hot combined feed-effluent (HCFE) exchanger. The cold stream, a combination of vapor feed with hydrogen rich recycle gas, is introduced into a HCFE exchanger and is heated. (Entrance temperature: 39.7° C. Exit temperature: 533.7° C.) The feed/recycle exits the HCFE as a gas and goes through a series of heating and reaction steps. The resulting product effluent or hot stream is introduced into the HCFE exchanger and is cooled down. (Entrance temperature: 583.7° C. Exit temperature: 142.3° C.) The effluent exits the HCFE exchanger and is then cooled down further using an air cooler. The effluent then passes through a dryer, separators, and strippers. Hydrogen recycle gas is separated after the dryer and returned to the feed stream.

Combined feed—effluent heat exchanger services are found in various process units (some examples are listed below), having different CFE process conditions. The entrance and exit temperatures of the heat exchangers depend on the feed composition, recycle gas, and product effluent as well as reaction conditions and process parameters. For example inlet/outlet temperatures may be:

a. Isomerization of xylenes:
   i. (Cold stream) Mix of Recycle Gas and Feed 143.1° C./401.0° C.
      1. H2 rich Recycle Gas 70.1° C.
      2. Liquid Feed 180.3° C.
   ii. (Hot stream) Reactor Effluent 443.9° C./166.6° C.
b. Transalkylation of toluene and other aromatics
   i. (Cold stream) Mix of Recycle Gas and Feed 112.5° C./457.9° C.
      1. H2 rich Recycle Gas 57.4° C.
      2. Liquid Feed 164.2° C.
   ii. (Hot stream) Reactor Effluent 492.9° C./136.9° C.
c. OLEFLEX CCFE in Cold Box: (Catalytic dehydrogenation—cold combined feed heat exchanger)
   i. (Cold stream) Mix of Recycle Gas and Feed −93.2° C./38.0° C.
      1. (Cold stream) H2 rich Recycle Gas −112.1° C.
      2. (Cold stream) Liquid Feed −89.2° C.
   ii. (Cold stream) Net Gas −121.6° C./27.4° C.
   iii. (Hot stream) Reactor Effluent 42.6° C./−92.0° C.

Heat exchangers may be made of any material of construction used in a chemical plant, refinery or petrochemical plant. Such construction material include carbon steel, stainless steel (typical for welded plates exchangers to manage thickness and strength), low chrome carbon steels, mid chrome carbon steels, austenitic stainless steels, high alloys, copper alloys, nickel alloys and titanium. Brazed aluminum exchangers are typically aluminum, and diffusion bonded exchangers are typically stainless steels.

Special devices may be used to obtain uniform distribution of liquid and vapor. In some exchangers, spray bars are used to spray and mix liquid feed into the vapor recycle gas as it enters the bundle. In a vertical tubular combined feed-effluent (VCFE) a spray pipe or liquid distributor provides a similar function. In a brazed aluminum or diffusion bonded exchanger spray holes or special fin geometry may be used to mix liquid and vapor streams (from separate inlet headers) at the inlet to the passages. In shell and tube exchangers, spray nozzles may be used to distribute a solvent (or wash water) into an exchanger to control fouling.

The spray bar or spray pipe may include covers or sleeves that can open and close holes that make up the spray nozzles. Operation of these covers can be maintained through use of a processor. The covers can be opened and closed to direct flow and restrict flow to different areas of the heat exchanger. In one aspect, a single cover will cover several holes at once. In another aspect, a single cover will cover only one hole.

Vertical CFE

Figure 3:
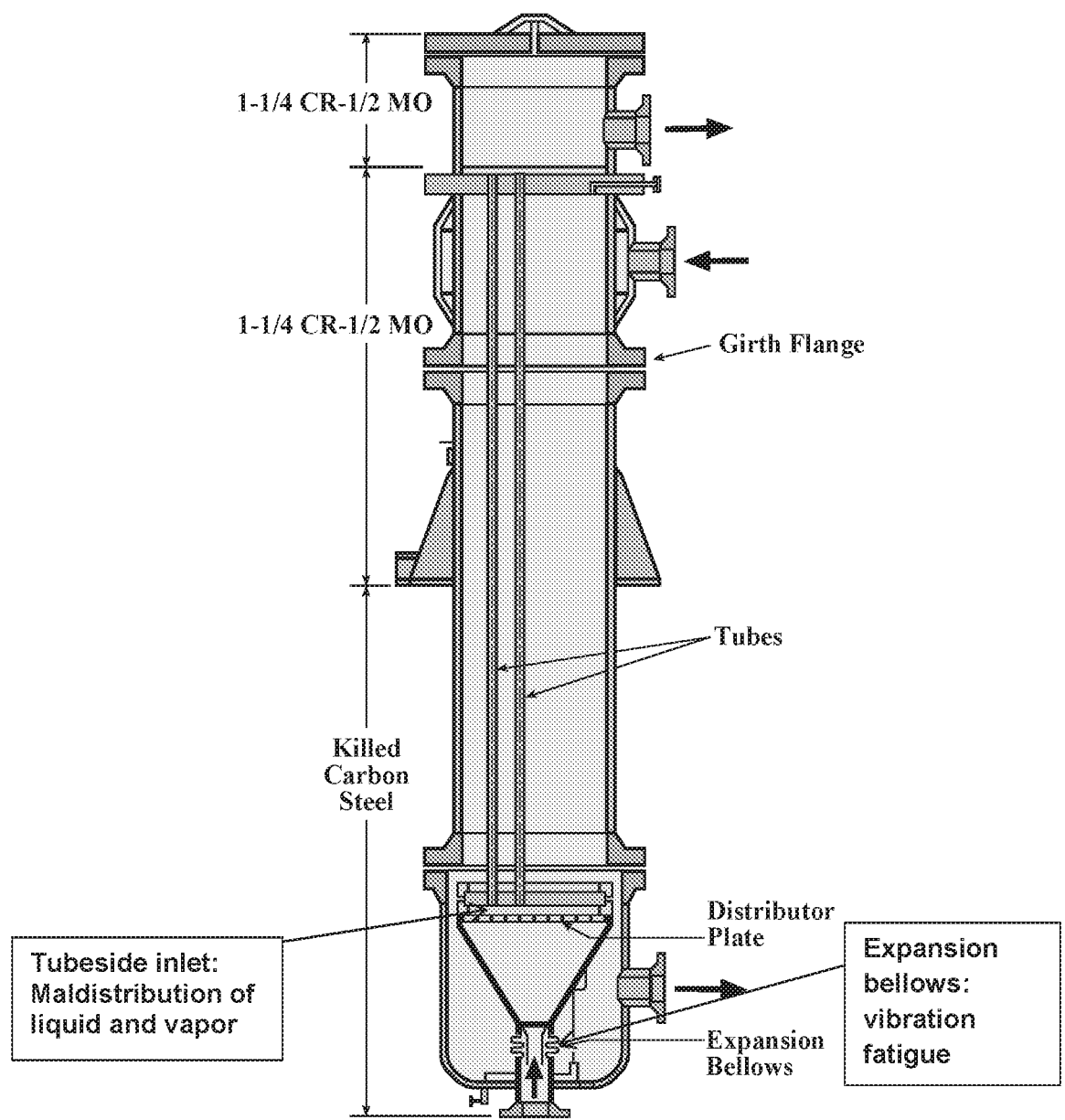
FIG. 3 depicts an illustrative a vertical CFE heat exchanger having a single tube pass design in accordance with one or more example embodiments.

FIG. 3 is an example of a vertical CFE heat exchanger having a single tube pass design. Typically, there is one shell in series but there may be multiple (1 to 4) shells in parallel. Normal operating heat transfer coefficient may be 35-50 Btu/hr-ft2-° F. Normal operating mean temperature difference may be about 80° F. Normal operating pressure drop may be 10.5-12.5 psi total.

Figure 4A:
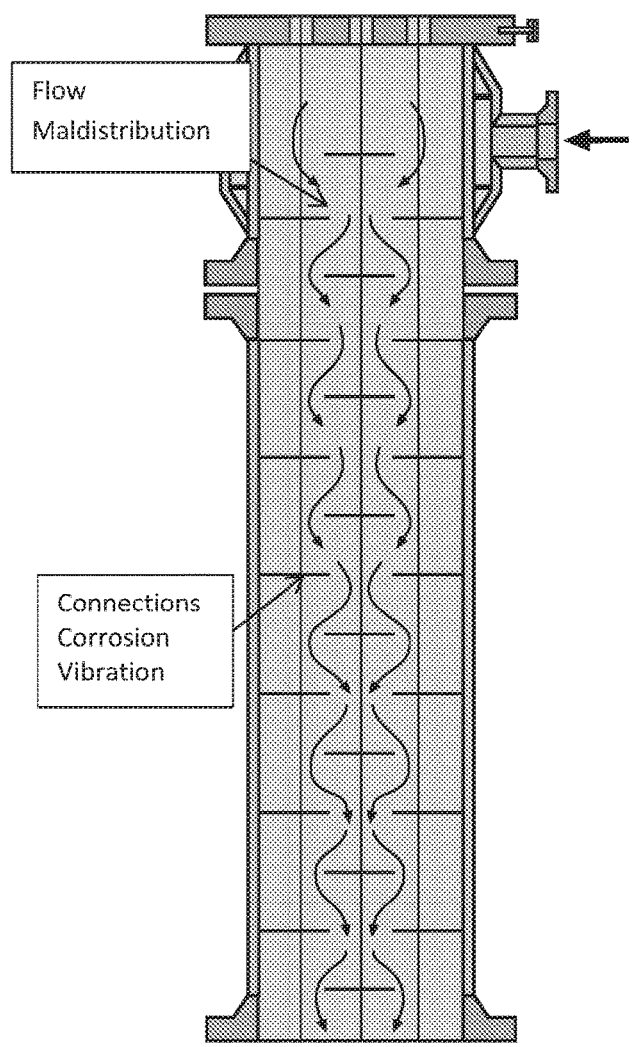
FIGS. 4A and 4B depict illustrative baffle arrangements that may be used in the heat exchanger of FIG. 3 in accordance with one or more example embodiments.
Figure 4B:
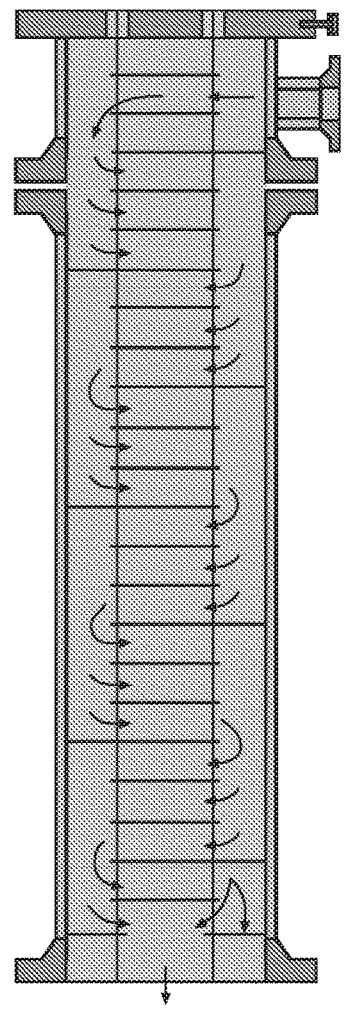

Expansion bellows are located inside the device adjacent the feed pipe inlet to accommodate expansion/contraction due to differential thermal expansion and fluctuating temperature conditions. The feed and recycle gas is distributed to the tubes via a spray pipe distributor and/or orifice plate. A shell side girth flange connects the upper and lower parts of the shell. The upper and lower parts are made of different metallurgy (e.g., CR/MO, carbon steel, respectively). The feed enters the bottom of the heat exchanger, flows through a distributor and through the tubes, and exits at the top. The product effluent enters at the top of the heat exchanger and has a circuitous path around baffle arrangements. Baffle arrangements may take various forms and constructions as seen in FIGS. 4A and 4B.

Although not as common, multiple shells may be used in series. In this case, by-pass pipes may be used in case one of the exchangers in the series must be taken offline, for example for maintenance.

Vertical HCFE

Known are vertical HCFE designs having a single tube pass design. Normal operating heat transfer coefficient may be 20-25 Btu/hr-ft2-° F. Normal operating mean temperature difference may be about 100° F. Normal operating pressure drop may be 2-3 psi total.

Expansion bellows are located inside the device adjacent the feed pipe inlet to accommodate expansion/contraction due to differential thermal expansion and fluctuating temperature conditions. A shell side girth flange connects upper and lower parts of the shell. The upper and lower parts are made of different metallurgy (e.g., stainless steel, carbon steel, respectively). The feed enters the bottom of the heat exchanger, has a circuitous path around baffle arrangements, and exits at the top. The product effluent enters at the top, flows through the tubes, and exits at the bottom.

PACKINOX Welded Plate Heat Exchanger

Also known are a PACKINOX welded plate heat exchanger with a single shell. Normal operating heat transfer coefficient may be two times or three times or more than the coefficients achieved with shell and tube type heat exchangers. Normal operating mean temperature difference may be less that about 60° F. Normal operating pressure drop may be 12.5 psi total.

Expansion bellows are located inside the device adjacent inlets and outlets to accommodate expansion/contraction due to differential thermal expansion and fluctuating temperature conditions. The feed and recycle gas enters the bottom of the device, flows in channels between plates, and exits at the top. The product effluent enters at the top, flows in different channels between the plates, and exits at the bottom.

A spray bar injection system may be used for distributing the liquid feed to channels between the plates and grids having holes to distribute the recycle gas to channels between the plates. The liquid is dispersed and the recycle gas carries the liquid upward between channels between the plates. Two spray bars are often used.

COMPLABLOC

The COMPLABLOC heat exchanger is typically used for chemically aggressive environments and low to moderate temperatures. The COMPLABLOC heat exchanger is a welded plate heat exchanger with no gaskets between the plates. The plates are welded alternatively to form channels. The frame has four corner girders, top and bottom heads and four side panels with nozzle connections. These components are bolted together and can be quickly taken apart for inspection, service or cleaning. This allows for compactness of surface yet is reasonably cleanable. The size and pressure, however, is somewhat restricted by the flat bolted covers that are needed. Flow enters the heat exchanger and is guided between alternating plates. The flow may be reversed several times until it exits at the other end of the heat exchanger. COMPABLOC exchangers are capable of obtaining higher heat transfer coefficients and smaller operating mean temperature differences with the similar pressure drops compared to shell and tube heat exchangers.

Multi-Stream Heat Exchangers

Multi-stream heat exchangers are configured so multiple streams are passed through the heat exchanger. A multi-stream service has more than two streams and may be more than 12 streams. Normal operating heat transfer coefficients, operating mean temperature differences and pressure drops depend on the individual streams being considered and will vary from stream to stream. They are typically similar to the values obtained in other plate type heat exchangers. Multi-stream heat exchangers include brazed aluminum plate fin heat exchangers (BAHX) and diffusion bonded heat exchangers.

A brazed aluminum plate fin heat exchangers (BAHX) is typically used for air separation and cryogenic applications. Brazed heat exchangers have very low service temperature limits and may have a multiple streams, as many as dozen or more streams, all chilled by a common cold stream or streams in one exchanger instead of multiple exchangers. Alternatively, multiple streams may all be heated by a common hot stream or streams in one exchanger.

Diffusion bonded heat exchangers are typically used for off-shore platform applications and include printed circuit heat exchangers (PCHE) and formed plate heat exchangers (FPHE.) Diffusion bonding is a solid state joining process which gives rise to parent metal strength via clean high temperature and pressure. The bonding does not involve melting or deformation and does not use braze, flux, or filler. The process promotes grain strength across the plate interface.

Shell & Tube Exchanger

Also known is a cross-flow floating tube sheet type shell and tube exchanger. This is a cross flow exchanger as the flow entering the shell takes a circuitous path around baffles and crossing over tubes carrying a flow across the exchanger. This exchanger has a four-pass flow on the tube side, and other quantities of tube side passes are possible. The tube may be a bundle of tubes that extend across the exchanger. The tubes extend between a stationary tube sheet and a floating tubesheet. The floating tubesheet and floating head cover allow for expansion and contraction of the tubes relative to the shell.

Spiral Plate Heat Exchanger

A spiral plate heat exchanger has two spiral channels that are concentric, one for each fluid. The curved channels provide great heat transfer and flow conditions for a wide variety of fluids. The spiral plate heal exchanger typically has a single passage for each fluid, making it a good choice for fouling fluids or fluids containing solid particles. The overall size of the unit is kept to a minimum therefore optimizing space. Spiral plate exchangers are easy to open to clean. Studs may be used to maintain plate spacing.

Vaporizers

FIGS. 5A and 5B depict bayonet type vaporizers. FIG. 5A depicts a typical vaporizer. A depicts an inlet for the process stream being vaporized. B is an outlet for the same stream. C is a vent. D and E represent level gauge and level control connections respectively. F is a side drain. Steam enters through H. Condensate is removed through G via chest drain.

FIG. 5B depicts a bayonet type tube. Steam enters the inner tube and flows upward. The top of the inner tube is open so the steam flows downward in the annular space. The steam is condensed in this area. The level liquid level (condensate) is controlled below top of bayonet tubes. A small amount of vapor superheat is possible as a portion of the bayonet tube extends above the liquid level and continues to heat the vaporized process stream.

Problems Encountered-Generally

Heat exchangers are subjected to various issues, including but not limited to maldistribution, thermal stress, fouling, strain, vibrations, and corrosion, which can affect their performance or result in cross leakage and ultimately failure of components of the heat exchange unit.

For example, corrosive agents in flow streams through the heat exchanger may corrode tubes or plates, compromising their integrity, resulting in cross-leaks or leaks to the outside. Fouling is the accumulation of unwanted substances on surfaces inside the tubes, outside the tubes, or on surfaces of plates. Fouling or formation of a thin coating adds resistance to heat transfer. Fouling can lead to plugging that can ultimately lead to higher pressure drop, reduced capacity or throughput, and to a blockage of the flow. Plugging may also occur from feed material that accumulates on the inside of tubes or channels. Fouling and plugging may also lead to flow maldistribution. Flow maldistribution may lead to poor performance, or to thermal stresses that can cause mechanical damage. Other damage potentially caused by fouling includes permanent damage to the exchanger bundle, where the insides of tubes, or outsides of tube, or plate channels cannot be effectively cleaned, in these cases, the exchanger, or the bundle, may need to be replaced. Damage to the process, for example not meeting product specifications, and damage to downstream equipment, for example fired heaters or reactors, may also result from fouling of a heat exchanger.

Mechanical damage, corrosion, failure of internal sealing devices, and thermal or mechanical stresses to the heat exchanger may all lead to cross-leakage, in particular in areas of connections between different parts and/or different metallurgies.

Tubes, plates, flanges, and pressure boundary materials may be subjected to strain due to thermal stresses. Thermal stresses are stresses caused by differential thermal growth between parts that are at different temperatures or of different materials, due to excessively high or low temperatures, or an excessive temperature differential (delta), or rapid changes in temperature conditions between streams in the heat exchanger, or maldistribution of flow within the heat exchanger (e.g., coolant flowing to some passages or tubes, and not to others).

Hot spots may form due to fouling, or maldistribution from many potential causes, and in addition to thermal stresses, may result in weakening and ultimately failure of the material.

Representative locations of, for example, possible maldistribution (uneven flow), corrosion, fouling, thermal stresses, potential corrosion or foulants, and vibration, are indicated in the figures. These are representative locations and not intended to be encompassing of all possible areas that may be subjected to various stresses or problems.

Monitoring

Monitoring the heat exchangers and the processes using heat exchangers may be performed to determine if problems are occurring, if equipment failures are imminent, if there is vibration, if there is maldistribution, if there is fouling, or the like. Monitoring also helps to collect data that can be correlated and used to predict behavior or problems in different heat exchangers used in the same plant or in other plants and/or processes.

There may or may not be anything that can be done to correct issues or problems associated with the issues in existing equipment, depending on the cause of the issues. In some aspects, process changes or operating conditions may be able to be altered to preserve the equipment until the next scheduled maintenance period. For example, streams may be monitored for corrosive contaminants, and pH may be monitored in order to predict higher than normal corrosion rates within the heat exchanger equipment. Tracking production rates, flow rates, and/or temperature may indicate issues with flows. For example, as fouling occurs, the production rate may fall if a specific outlet temperature can no longer be achieved at the targeted capacity and capacity has to be reduced to maintain the targeted outlet temperature.

Sensor Data Collection and Processing

Figure 6A:
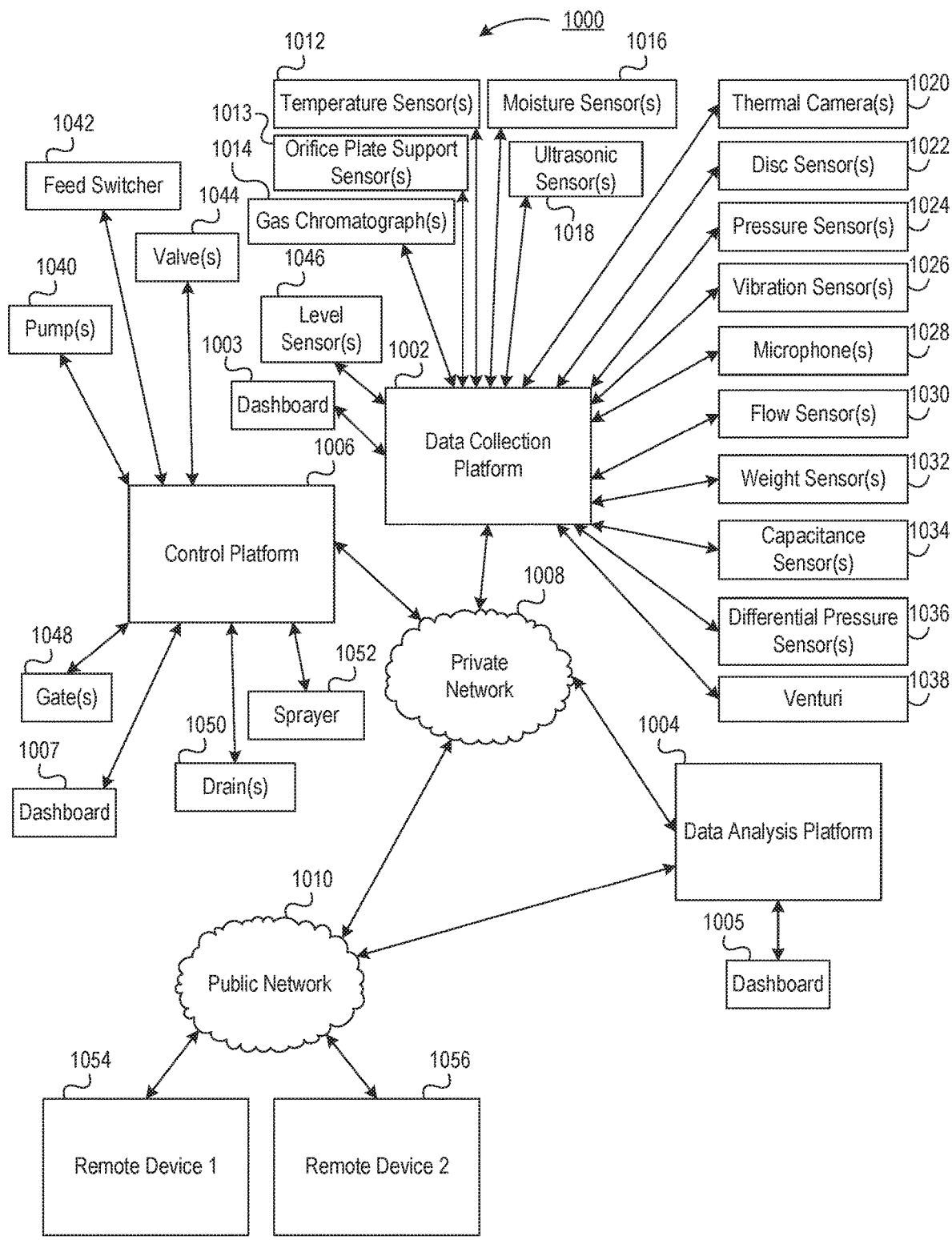
FIG. 6A depicts an illustrative computing environment for managing the operation of one or more pieces of equipment in a plant in accordance with one or more example embodiments.

The system may include one or more computing devices or platforms for collecting, storing, processing, and analyzing data from one or more sensors. FIG. 6A depicts an illustrative computing system that may be implemented at one or more components, pieces of equipment (e.g., heat exchanger), and/or plants. FIGS. 6A-6E (hereinafter collectively "FIG. 6"), show, by way of illustration, various components of the illustrative computing system in which aspects of the disclosure may be practiced. It is to be understood that other components may be used, and structural and functional modifications may be made, in one or more other embodiments without departing from the scope of the present disclosure. Moreover, various connections between elements are discussed in the following description, and these connections are general and, unless specified otherwise, may be direct or indirect, wired or wireless, and/or combination thereof, and that the specification is not intended to be limiting in this respect.

FIG. 6A depicts an illustrative operating environment in which various aspects of the present disclosure may be implemented in accordance with example embodiments. The computing system environment 1000 illustrated in FIG. 6A is only one example of a suitable computing environment and is not intended to suggest any limitation as to the scope of use or functionality contained in the disclosure. The computing system environment 1000 may include various sensor, measurement, and data capture systems, a data collection platform 1002, a data analysis platform 1004, a control platform 1006, one or more networks, one or more remote devices 1054, 1056, and/or one or more other elements. The numerous elements of the computing system environment of FIG. 6A may be communicatively coupled through one or more networks. For example, the numerous platforms, devices, sensors, and/or components of the computing system environment may be communicatively coupled through a private network 1008. The sensors be positioned on various components in the plant and may communicate wirelessly or wired with one or more platforms illustrated in FIG. 6A. The private network 1008 may include, in some examples, a network firewall device to prevent unauthorized access to the data and devices on the private network 1008. Alternatively or additionally, the private network 1008 may be isolated from external access through physical means, such as a hard-wired network with no external, direct access point. The data communicated on the private network 1008 may be optionally encrypted for further security. Depending on the frequency of collection and transmission of sensor measurements and other data to the data collection platform 1002, the private network 1008 may experience large bandwidth usage and be technologically designed and arranged to accommodate for such technological issues. Moreover, the computing system environment 1000 may also include a public network 1010 that may be accessible to remote devices (e.g., remote device 1054, remote device 1056). In some examples, a remote device may be located not in the proximity (e.g., more than one mile away) of the various sensor, measurement, and data capture systems illustrated in FIG. 6A. In other examples, the remote device may be physically located inside a plant, but restricted from access to the private network 1008; in other words, the adjective "remote," need not necessarily require the device to be located at a great distance from the sensor systems and other components.

Although the computing system environment of FIG. 6A illustrates logical block diagrams of numerous platforms and devices, the disclosure is not so limited. In particular, one or more of the logical boxes in FIG. 6 may be combined into a single logical box or the functionality performed by a single logical box may be divided across multiple existing or new logical boxes. For example, aspects of the functionality performed by the data collection platform 1002 may be incorporated into one or each of the sensor devices illustrated in FIG. 6A. As such, the data collection may occur local to the sensor device, and the enhanced sensor system may communicate directly with one or more of the control platform 1006 and/or data analysis platform 1004. An illustrative example of such an embodiment is contemplated by FIG. 6A. Moreover, in such an embodiment, the enhanced sensor system may measure values common to a sensor, but may also filter the measurements such just those values that are statistically relevant or of-interest to the computing system environment are transmitted by the enhanced sensor system. As a result, the enhanced sensor system may include a processor (or other circuitry that enables execution of computer instructions) and a memory to store those instructions and/or filtered data values. The processor may be embodied as an application-specific integrated circuit (ASIC), FPGA, or other hardware- or software-based module for execution of instructions. In another example, one or more sensors illustrated in FIG. 6A may be combined into an enhanced, multi-purpose sensor system. Such a combined sensor system may provide economies of scale with respect to hardware components such as processors, memories, communication interfaces, and others.

In yet another example, the data collection platform 1002 and data analysis platform 1004 may reside on a single server computer and depicted as a single, combined logical box on a system diagram. Moreover, a data store may be illustrated in FIG. 6A separate and apart from the data collection platform 1002 and data analysis platform 1004 to store a large amount of values collected from sensors and other components. The data store may be embodied in a database format and may be made accessible to the public network 1010; meanwhile, the control platform 1006, data collection platform 1002, and data analysis platform 1004 may be restricted to the private network 1008 and left inaccessible to the public network 1010. As such, the data collected from a plant may be shared with users (e.g., engineers, data scientists, others), a company's employees, and even third parties (e.g., subscribers to the company's data feed) without compromising potential security requirements related to operation of a plant. The data store may be accessible to one or more users and/or remote devices over the public network 1010.

Referring to FIG. 6A, process measurements from various sensor and monitoring devices may be used to monitor conditions in, around, and on process equipment (e.g., heat exchanger). Such sensors may include, but are not limited to, pressure sensors 1024, differential pressure sensors 1036, various flow sensors (including but not limited to orifice plate type 1013, disc sensors 1022, venturi 1038, other flow sensors 1030), temperature sensors 1012 including thermal cameras 1020 and skin thermocouples, capacitance sensors 1034, weight sensors 1032, gas chromatographs 1014, moisture sensors 1016, ultrasonic sensors 1018, position sensors, timing sensors, vibration sensors 1026, microphones 1028, level sensors 1046, liquid level (hydraulic fluid) sensors, and other sensors used in the refining and petrochemical industry. Further, process laboratory measurements may be taken using gas chromatographs 1014, liquid chromatographs, distillation measurements, octane measurements, and other laboratory measurements. System operational measurements also can be taken to correlate the system operation to the heat exchanger measurements.

In addition, sensors may include transmitters and/or deviation alarms. One or more sensors may be programmed to set off an alarm or alert. For example, if an actuator fails, sensor data may be used to automatically trigger an alarm or alert (e.g., an audible alarm or alert, a visual alarm or alert). Other sensors may transmit signals to a processor or a hub that collects the data and sends to a processor. For example, temperature and pressure measurements may be sent to a hub (e.g., data collection platform 1002). In one or more embodiments, temperature sensors 1012 may include thermocouples, fiber optic temperature measurement, thermal cameras 1020, and/or infrared cameras. Skin thermocouples may be applied to heat exchanger casing, or alternatively, to tubes, plates, or placed directly on a wall of a heat exchanger component. Alternatively, thermal (infrared) cameras 1020 may be used to detect temperature (e.g., hot spots) in all aspects of the equipment, including bundles (tubes). A shielded (insulated) tube skin thermocouple assembly may be used to obtain accurate measurements. One example of a thermocouple may be a removable XTRACTO Pad. A thermocouple can be replaced without any additional welding. Clips and/or pads may be used for ease of replacement. Fiber Optic cable can be attached to the pipe, line, and/or vessel to provide a complete profile of temperatures.

Returning to FIG. 4A, sensors may be also used throughout a plant or heat exchanger to detect and monitor various issues such as maldistribution, thermal stresses, vibration, fouling, and plugging. Sensors might be able to detect whether feed composition into the exchanger, such as pH, are outside of acceptable ranges leading to a corrosive environment or whether consumption of sacrificial anodes (in water services) is nearing completion and resulting in a corrosive environment. Sensors detecting outlet temperatures and pressure drops may be used to determine/predict flow and production rate changes.

Furthermore, flow sensors may be used in flow paths such as the inlet to the path, outlet from the path, or within the path. If multiple tubes are used, the flow sensors may be placed in corresponding positions in each of the tubes. In this manner, one can determine if one of the tubes is behaving abnormally compared to one or more other tubes. Flow may be determined by pressure-drop across a known resistance, such as by using pressure taps. Other types of flow sensors include, but are not limited to, ultrasonic, turbine meter, hot wire anemometer, vane meter, Kármán™, vortex sensor, membrane sensor (membrane has a thin film temperature sensor printed on the upstream side, and one on the downstream side), tracer, radiographic imaging (e.g., identify two-phase vs. single-phase region of channels), an orifice plate (e.g., which may, in some examples, be placed in front of or be integral to one or more tubes or channels), pitot tube, thermal conductivity flow meter, anemometer, internal pressure flow profile, and/or measure cross tracer (measuring when the flow crosses one plate and when the flow crosses another plate).

The effect of flow vibrations may be detected and/or corrected. If the flow through the exchanger is not uniform, then high flow velocities can cause local vibration. This vibration can damage parts of the exchanger, such as tube, by many mechanisms, leading to leakage or cross-leakage of exchangers. Flow-induced vibration is a large source of failure in shell and tube heat exchangers. Fluttering or resonance in the tubes may cause vibration. In addition, equipment-induced vibration, such as mechanical vibration (e.g., from nearby equipment, such as air compressors or refrigeration machines, or from loose support structures) can cause a variety of damage. For example, welded pieces may crack or break loose. Mechanical vibration can cause tube failures (e.g., in the form of a fatigue stress crack or erosion of tubing at the point of contact with baffles). Flow vibration can lead to mal-distribution and cross-leakage. Flow vibration can accelerate dislodging of corrosion particles leading to further corrosion or blocked flow. Flow vibration may ultimately crack plates, tubes, and baffles. Vibration may be detected with vibration sensors attached to the equipment such as plates, tubes, baffles, or shells. Flow vibration may further be detected using flow and pressure sensors in order to detect abnormalities in flow and pressure drop. In some embodiments, an enhanced sensor system may comprise numerous of the aforementioned sensors in a single system component to provide improved sensory measurements and analytics.

In another example, strain sensors may measure the strain on a part. For example, a strain gauge may be built into heat exchanger plates and headers. Measurements from such gauges may indicate whether a plate may be getting ready to leak (pre-leakage), provide a prediction of cross-leakage, or fail completely. Electrical strain gauges, for example, are thin, rectangular-shaped strips of foil with maze-like wiring patterns on them leading to a couple of electrical cables. A strain gauge may be more sensitive in a particular direction (e.g., a strain gauge may be more sensitive in a horizontal direction than a vertical direction, or may be more sensitive in a vertical direction than a horizontal direction). A strain gauge may include an electrical conductor (e.g., foil, semiconductor, or nanoparticle). The electrical conductor is applied to a component. When the component is strained, its width is changed. Specifically, for example, when the electrical conductor is subjected to a strain (e.g., compression or stretching) in a particular direction, the electrical conductor may increase or decrease in electrical conductivity. The gauge's resistance will experience a corresponding change (increased or decreased electrical conductivity), which allows for an amount of induced stress on the strain gauge to be determined when a voltage is applied to the gauge.

Sensor data, process measurements, and/or calculations made using the sensor data or process measurements may be used to monitor and/or improve the performance of the equipment and parts making up the equipment, as discussed in further detail below. For example, sensor data may be used to detect that a desirable or an undesirable chemical reaction is taking place within a particular piece of equipment, and one or more actions may be taken to encourage or inhibit the chemical reaction. Chemical sensors may be used to detect the presence of one or more chemicals or components in the streams, such as corrosive species, oxygen, hydrogen, and/or water (moisture). Chemical sensors may use gas chromatographs, liquid chromatographs, distillation measurements, and/or octane measurements. In another example, equipment information, such as wear, efficiency, production, state, or other condition information, may be gathered and determined based on sensor data. Corrective action may be taken based on determining this equipment information. For example, if the equipment is showing signs of wear or failure, corrective actions may be taken, such as taking an inventory of parts to ensure replacement parts are available, ordering replacement parts, and/or calling in repair personnel to the site. Certain parts of equipment may be replaced immediately. Other parts may be safe to use, but a monitoring schedule may be adjusted. Alternatively or additionally, one or more inputs or controls relating to a process may be adjusted as part of the corrective action. These and other details about the equipment, sensors, processing of sensor data, and actions taken based on sensor data are described in further detail below.

Monitoring the heat exchangers and the processes using heat exchangers includes collecting data that can be correlated and used to predict behavior or problems in different heat exchangers used in the same plant or in other plants and/or processes. Data collected from the various sensors (e.g., measurements such as flow, pressure drop, thermal performance, vessel skin temperature at the top, expansion bellows leak, vibration, etc.) may be correlated with external data, such as environmental or weather data. Process changes or operating conditions may be able to be altered to preserve the equipment until the next scheduled maintenance period. Fluids may be monitored for corrosive contaminants and pH may be monitored in order to predict higher than normal corrosion rates within the heat exchanger equipment. At a high level, sensor data collected (e.g., by the data collection platform) and data analysis (e.g., by the data analysis platform) may be used together, for example, for process simulation, equipment simulation, and/or other tasks. For example, sensor data may be used for process simulation and reconciliation of sensor data. The resulting, improved process simulation may provide a stream of physical properties that are used to calculate heat flow, etc. These calculations may lead to thermal and pressure drop performance prediction calculations for specific equipment, and comparisons of equipment predictions to observations from the operating data (e.g., predicted/expected outlet temperature and pressure vs. measured outlet temperature and pressure). This causes identification of one or more of fouling, maldistribution, and/or other issues that eventually lead to a potential control changes and/or recommendation etc.

Systems Facilitating Sensor Data Collection

Sensor data may be collected by a data collection platform 1002. The sensors may interface with the data collection platform 1002 via wired or wireless transmissions. The data collection platform 1002 may continuously or periodically (e.g., every second, every minute, every hour, every day, once a week, once a month) transmit collected sensor data to a data analysis platform 1004, which may be nearby or remote from the data collection platform 1002.

Sensor data (e.g., temperature data) may be collected continuously or at periodic intervals (e.g., every second, every five seconds, every ten seconds, every minute, every five minutes, every ten minutes, every hour, every two hours, every five hours, every twelve hours, every day, every other day, every week, every other week, every month, every other month, every six months, every year, or another interval). Data may be collected at different locations at different intervals. For example, data at a known hot spot may be collected at a first interval, and data at a spot that is not a known hot spot may be collected at a second interval. The data collection platform may transmit collected sensor data to a data analysis platform, which may be nearby or remote from the data collection platform.

Figure 6B:
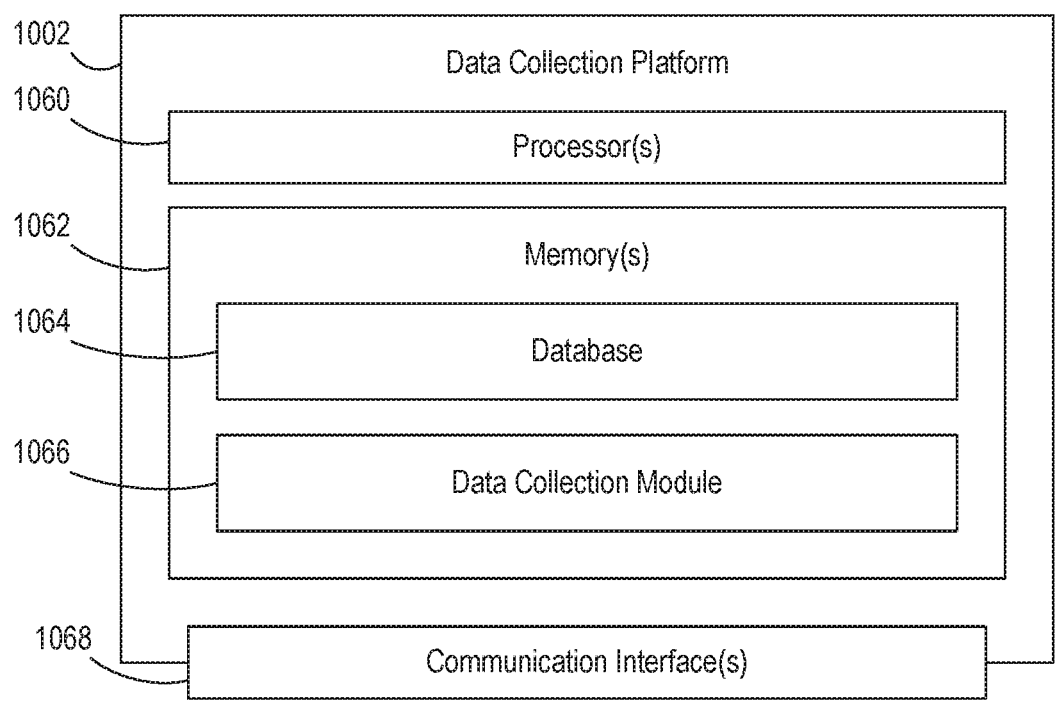
FIG. 6B depicts an illustrative data collection computing platform for collecting data related to the operation of one or more pieces of equipment in a plant in accordance with one or more example embodiments.
Figure 6C:
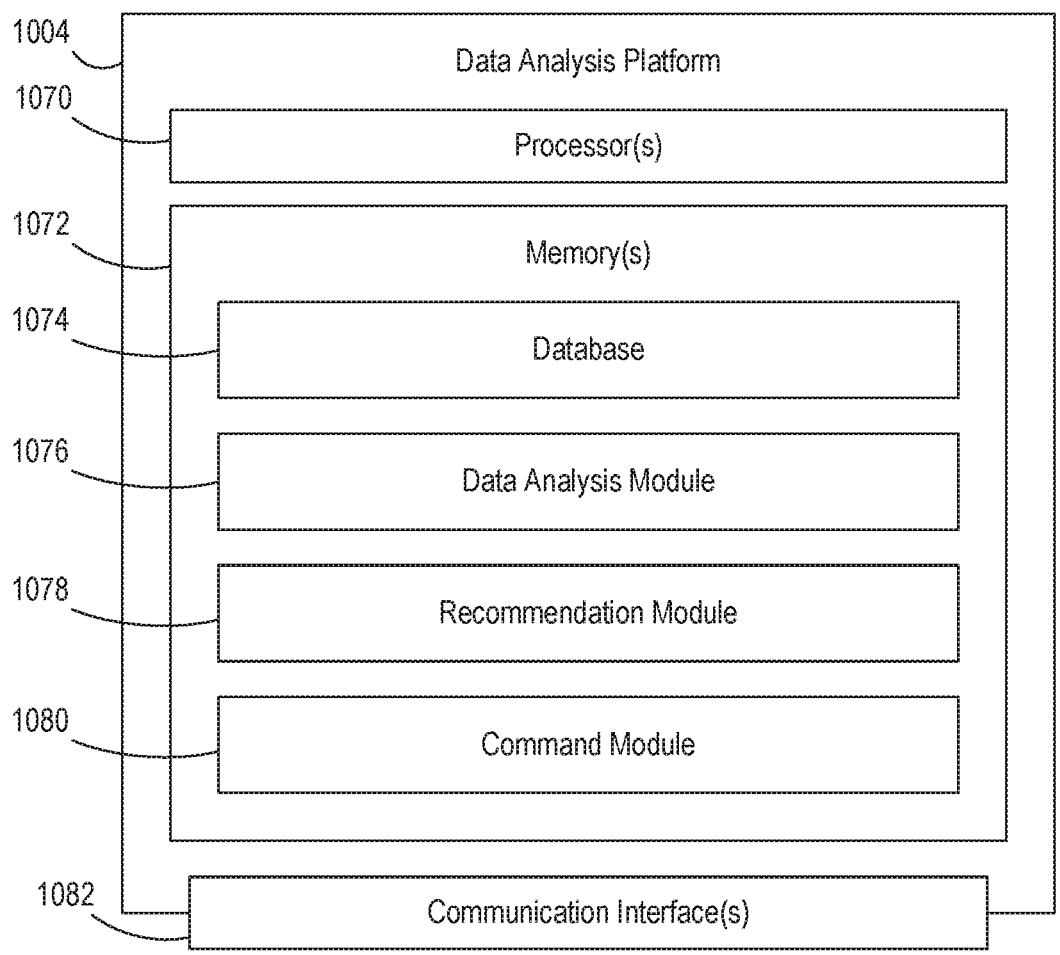
FIG. 6C depicts an illustrative data analysis computing platform for analyzing data related to the operation of one or more pieces of equipment in a plant in accordance with one or more example embodiments.
Figure 6D:
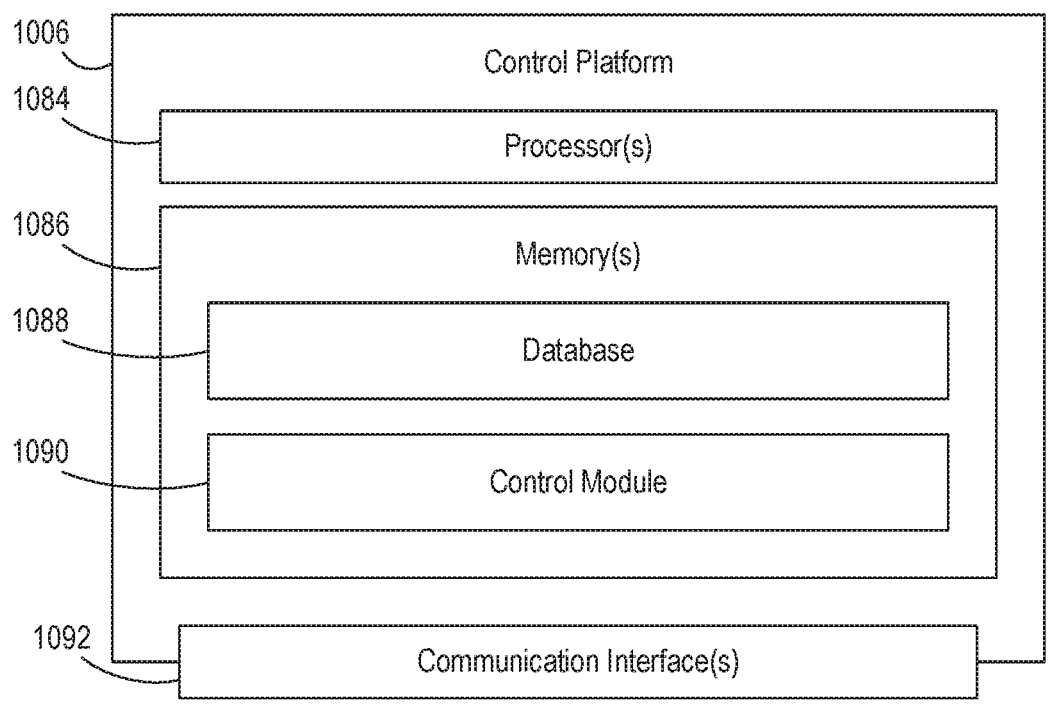
FIG. 6D depicts an illustrative data analysis computing platform for analyzing data related to the operation of one or more pieces of equipment in a plant in accordance with one or more example embodiments.
Figure 6E:
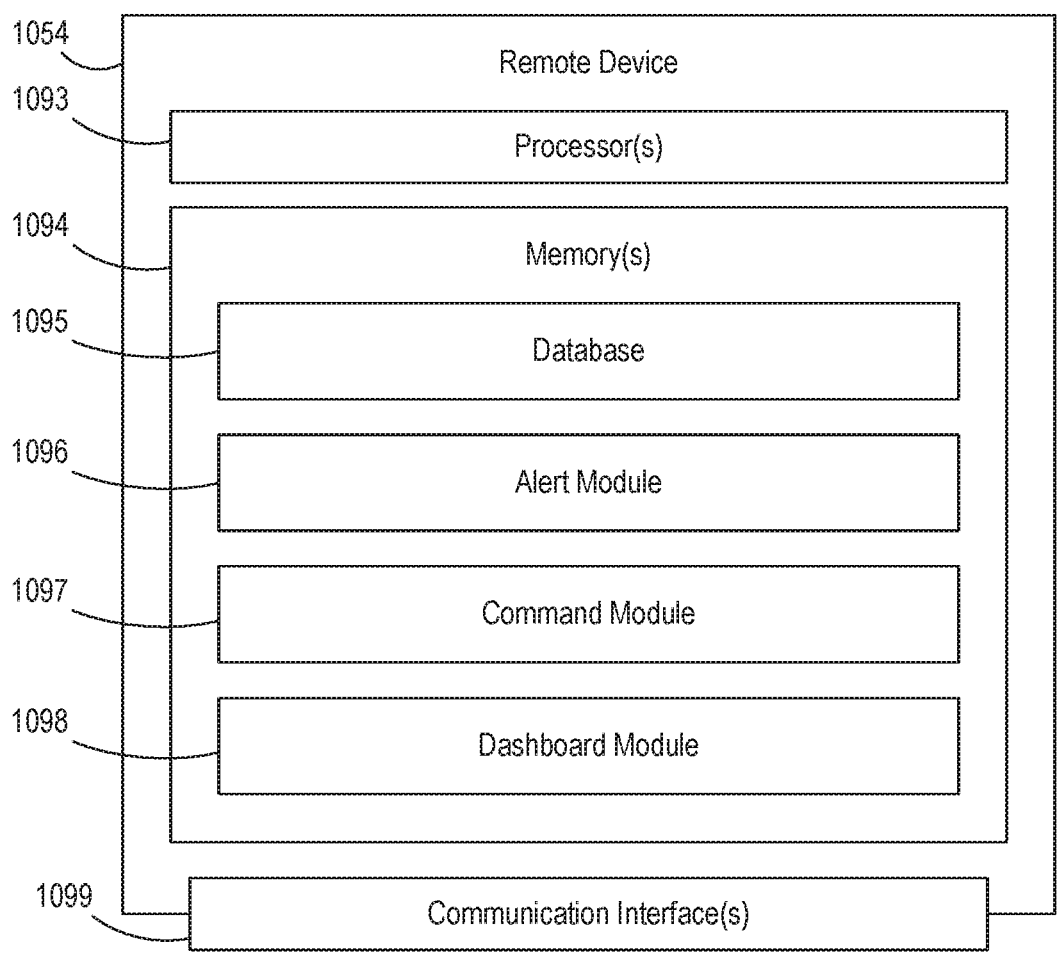
FIG. 6E depicts an illustrative control computing platform for controlling one or more parts of one or more pieces of equipment in a plant in accordance with one or more example embodiments.

The computing system environment of FIG. 6A includes logical block diagrams of numerous platforms and devices that are further elaborated upon in FIG. 6B, FIG. 6C, FIG. 6D, and FIG. 6E. FIG. 6B is an illustrative data collection platform 1002. FIG. 6C is an illustrative data analysis platform 1004. FIG. 6D is an illustrative control platform 1006. FIG. 6E is an illustrative remote device 1054. These platforms and devices of FIG. 6 include one or more processing units (e.g., processors) to implement the methods and functions of certain aspects of the present disclosure in accordance with the example embodiments. The processors may include general-purpose microprocessors and/or special-purpose processors designed for particular computing system environments or configurations. For example, the processors may execute computer-executable instructions in the form of software and/or firmware stored in the memory of the platform or device. Examples of computing systems, environments, and/or configurations that may be suitable for use with the disclosed embodiments include, but are not limited to, personal computers (PCs), server computers, hand-held or laptop devices, smart phones, multiprocessor systems, microprocessor-based systems, programmable consumer electronics, network PCs, minicomputers, mainframe computers, distributed computing environments that include any of the above systems or devices, and the like.

In addition, the platform and/or devices in FIGS. 6A and 6B may include one or more memories include any of a variety of computer-readable media. Computer-readable media may be any available media that may be accessed by the data collection platform 1002, may be non-transitory, and may include volatile and nonvolatile, removable and non-removable media implemented in any method or technology for storage of information such as computer-readable instructions, object code, data structures, database records, program modules, or other data. Examples of computer-readable media may include random access memory (RAM), read only memory (ROM), electronically erasable programmable read only memory (EEPROM), flash memory or other memory technology, compact disk read-only memory (CD-ROM), digital versatile disks (DVD) or other optical disk storage, magnetic cassettes, magnetic tape, magnetic disk storage or other magnetic storage devices, or any other medium that can be used to store the desired information and that can be accessed by the data collection platform 1002. The memories in the platform and/or devices may further store modules that may include compiled software code that causes the platform, device, and/or overall system to operate in a technologically improved manner as disclosed herein. For example, the memories may store software used by a computing platform, such as operating system, application programs, and/or associated database.

Furthermore, the platform and/or devices in FIGS. 6A and 6B may include one or more communication interfaces including, but are not limited to, a microphone, keypad, keyboard, touch screen, and/or stylus through which a user of a computer (e.g., a remote device) may provide input, and may also include a speaker for providing audio output and a video display device for providing textual, audiovisual and/or graphical output. Input may be received via one or more graphical user interfaces, which may be part of one or more dashboards (e.g., dashboard 1003, dashboard 1005, dashboard 1007). The communication interfaces may include a network controller for electronically communicating (e.g., wirelessly or wired) over a public network 1010 or private network 1008 with one or more other components on the network. The network controller may include electronic hardware for communicating over network protocols, including TCP/IP, UDP, Ethernet, and other protocols.

In some examples, one or more sensor devices in FIG. 6A may be enhanced by incorporating functionality that may otherwise be found in a data collection platform 1002. These enhanced sensor system may provide further filtering of the measurements and readings collected from their sensor devices. For example, with some of the enhanced sensor systems in the operating environment illustrated in FIG. 6A, an increased amount of processing may occur at the sensor so as to reduce the amount of data needing to be transferred over a private network 1008 in real-time to a computing platform. The enhanced sensor system may filter at the sensor itself the measured/collected/captured data and only particular, filtered data may be transmitted to the data collection platform 1002 for storage and/or analysis.

Referring to FIG. 6B, in one or more embodiments, a data collection platform 1002 may include one or more processors 1060, one or more memories 1062, and communication interfaces 1068. The memory 1062 may include a database 1064 for storing data records of various values collected from one or more sources. In addition, a data collection module 1066 may be stored in the memory 1062 and assist the processor 1060 in the data collection platform 1002 in communicating with, via the communications interface 1068, one or more sensor, measurement, and data capture systems, and processing the data received from these sources. In some embodiments, the data collection module 1066 may include computer-executable instructions that, when executed by the processor 1060, cause the data collection platform 1002 to perform one or more of the steps disclosed herein. In other embodiments, the data collection module 1066 may be a hybrid of software-based and/or hardware-based instructions to perform one or more of the steps disclosed herein. In some examples, the data collection module 1066 may assist an enhanced sensor system with further filtering the measurements and readings collected from the sensor devices. Although the elements of FIG. 6B are illustrated as logical block diagrams, the disclosure is not so limited. In particular, one or more of the logical boxes in FIG. 6B may be combined into a single logical box or the functionality performed by a single logical box may be divided across multiple existing or new logical boxes. Moreover, some logical boxes that are visually presented as being inside of another logical box may be moved such that they are partially or completely residing outside of that logical box. For example, while the database 1064 in FIG. 6B is illustrated as being stored inside one or more memories 1062 in the data collection platform 1002, FIG. 6B contemplates that the database 1064 may be stored in a standalone data store communicatively coupled to the data collection module 1066 and processor 1060 of the data collection platform 1002 via the communications interface 1068 of the data collection platform 1002.

In addition, the data collection module 1066 may assist the processor 1060 in the data collection platform 1002 in communicating with, via the communications interface 1068, and processing data received from other sources, such as data feeds from third-party servers and manual entry at the field site from a dashboard graphical user interface (e.g., via dashboard 1003). For example, a third-party server may provide contemporaneous weather data to the data collection module. Some elements of chemical and petrochemical/refinery plants may be exposed to the outside and thus may be exposed to various environmental stresses. Such stresses may be weather related such as temperature extremes (hot and cold), high wind conditions, and precipitation conditions such as snow, ice, and rain. Other environmental conditions may be pollution particulates such as dust and pollen, or salt if located near an ocean, for example. Such stresses can affect the performance and lifetime of equipment in the plants. Different locations may have different environmental stresses. For example, a refinery in Texas will have different stresses than a chemical plant in Montana. In another example, data manually entered from a dashboard graphical user interface (e.g., via dashboard 1003) (or other means) may be collected and saved into memory by the data collection module. Production rates may be entered and saved in memory. Tracking production rates may indicate issues with flows. For example, as fouling occurs, the production rate may fall if a specific outlet temperature can no longer be achieved at the targeted capacity and capacity has to be reduced to maintain the targeted outlet temperature.

Referring to FIG. 6C, in one or more embodiments, a data analysis platform 1004 may include one or more processors 1070, one or more memories 1072, and communication interfaces 1082. The memory 1072 may include a database 1074 for storing data records of various values collected from one or more sources. Alternatively or additionally, the database 1074 may be the same database as that depicted in FIG. 6B and the data analysis platform 1004 may communicatively couple with the database 1074 via the communication interface of the data analysis platform 1004. At least one advantage of sharing a database between the two platforms is the reduced memory requirements due to not duplicating the same or similar data. In addition, a data analysis module 1076 may be stored in the memory 1072 and assist the processor 1070 in the data analysis platform 1004 in processing and analyzing the data values stored in the database 1074. In some embodiments, the data analysis module 1076 may include computer-executable instructions that, when executed by the processor 1070, cause the data analysis platform 1004 to perform one or more of the steps disclosed herein. In other embodiments, the data analysis module 1076 may be a hybrid of software-based and/or hardware-based instructions to perform one or more of the steps disclosed herein. In some embodiments, the data analysis module 1076 may perform statistical analysis, predictive analytics, and/or machine learning on the data values in the database 1074 to generate predictions and models. For example, the data analysis platform 1004 may analyze sensor data to detect new hot spots and/or to monitor existing hot spots (e.g., to determine if an existing hot spot is growing, maintaining the same size, or shrinking) in the equipment of a plant. The data analysis platform 1004 may compare temperature or other data from different dates to determine if changes are occurring. Such comparisons may be made on a monthly, weekly, daily, hourly, real-time, or some other basis.

Referring to FIG. 6C, the recommendation module 1078 in the data analysis platform 1004 may coordinate with the data analysis module 1076 to generate recommendations for adjusting one or more parameters for the operation of the plant environment depicted in FIG. 6A. In some embodiments, the recommendation module 1078 may communicate the recommendation to the command module 1080, which may generate command codes that may be transmitted, via the communications interface, to cause adjustments or halting/starting of one or more operations in the plant environment. The command codes may be transmitted to a control platform 1006 for processing and/or execution. In one or more embodiments, the command codes may be directly communicated, either wirelessly or in a wired fashion, to physical components at the plant such that the physical components include an interface to receive the commands and execute on them.

Although the elements of FIG. 6C are illustrated as logical block diagrams, the disclosure is not so limited. In particular, one or more of the logical boxes in FIG. 6C may be combined into a single logical box or the functionality performed by a single logical box may be divided across multiple existing or new logical boxes. Moreover, some logical boxes that are visually presented as being inside of another logical box may be moved such that they are partially or completely residing outside of that logical box. For example, while the database is visually depicted in FIG. 6C as being stored inside one or more memories in the data analysis platform 1004, FIG. 6C contemplates that the database may be stored in a standalone data store communicatively coupled to the data analysis module and processor of the data analysis platform 1004 via the communications interface of the data analysis platform 1004. Furthermore, the databases from multiple plant locations may be shared and holistically analyzed to identify one or more trends and/or patterns in the operation and behavior of the plant and/or plant equipment. In such a crowdsourcing-type example, a distributed database arrangement may be provided where a logical database may simply serve as an interface through which multiple, separate databases may be accessed. As such, a computer with predictive analytic capabilities may access the logical database to analyze, recommend, and/or predict the behavior of one or more aspects of plants and/or equipment. In another example, the data values from a database from each plant may be combined and/or collated into a single database where predictive analytic engines may perform calculations and prediction models.

Referring to FIG. 6D, in one or more embodiments, a control platform 1006 may include one or more processors 1084, one or more memories 1086, and communication interfaces 1092. The memory 1086 may include a database 1088 for storing data records of various values transmitted from a user interface, computing device, or other platform. The values may include parameter values for particular equipment at the plant. For example, some illustrative equipment at the plant that may be configured and/or controlled by the control platform 1006 include, but is not limited to, a feed switcher 1042, sprayer 1052, one or more valves 1044, one or more pumps 1040, one or more gates 1048, and/or one or more drains 1050. In addition, a control module 1090 may be stored in the memory and assist the processor in the control platform 1006 in receiving, storing, and transmitting the data values stored in the database. In some embodiments, the control module 1090 may include computer-executable instructions that, when executed by the processor 1084, cause the control platform 1006 to perform one or more of the steps disclosed herein. In other embodiments, the control module may be a hybrid of software-based and/or hardware-based instructions to perform one or more of the steps disclosed herein.

In a plant environment such as illustrated in FIG. 6A, if sensor data is outside of a safe range, this may be cause for immediate danger. As such, there may be a real-time component to the system such that the system processes and responds in a timely manner. Although in some embodiments, data could be collected and leisurely analyzed over a lengthy period of months, numerous embodiments contemplate a real-time or near real-time responsiveness in analyzing and generating alerts, such as those generated or received by the alert module in FIG. 6E.

Referring to FIG. 6E, in one or more embodiments, a remote device 1054 may include one or more processors 1093, one or more memories 1094, and communication interfaces 1099. The memory 1094 may include a database 1095 for storing data records of various values entered by a user or received through the communications interface. In addition, an alert module 1096, command module 1097, and/or dashboard module 1098 may be stored in the memory 1094 and assist the processor 1093 in the remote device 1054 in processing and analyzing the data values stored in the database. In some embodiments, the aforementioned modules may include computer-executable instructions that, when executed by the processor, cause the remote device 1054 to perform one or more of the steps disclosed herein. In other embodiments, the aforementioned modules may be a hybrid of software-based and/or hardware-based instructions to perform one or more of the steps disclosed herein. In some embodiments, the aforementioned modules may generate alerts based on values received through the communications interface. The values may indicate a dangerous condition or even merely a warning condition due to odd sensor readings. The command module 1097 in the remote device 1054 may generate a command that when transmitted through the communications interface to the platforms at the plant, causes adjusting of one or more parameter operations of the plant environment depicted in FIG. 6A. In some embodiments, the dashboard module 1098 may display a graphical user interface to a user of the remote device 1054 to enable the user to enter desired parameters and/or commands. These parameters/commands may be transmitted to the command module 1097 to generate the appropriate resulting command codes that may be then transmitted, via the communications interface, to cause adjustments or halting/starting of one or more operations in the plant environment. The command codes may be transmitted to a control platform 1006 for processing and/or execution. In one or more embodiments, the command codes may be directly communicated, either wirelessly or in a wired fashion, to physical components at the plant such that the physical components include an interface to receive the commands and execute them.

Although FIG. 6E is not so limited, in some embodiments the remote device 1054 may include a desktop computer, a smartphone, a wireless device, a tablet computer, a laptop computer, and/or the like. The remote device 1054 may be physically located locally or remotely, and may be connected by one of communications links to the public network 1010 that is linked via a communications link to the private network 1008. The network used to connect the remote device 1054 may be any suitable computer network including the Internet, an intranet, a wide-area network (WAN), a local-area network (LAN), a wireless network, a digital subscriber line (DSL) network, a frame relay network, an asynchronous transfer mode (ATM) network, a virtual private network 1008 (VPN), or any combination of any of the same. Communications links may be any communications links suitable for communicating between workstations and server, such as network links, dial-up links, wireless links, hard-wired links, as well as network types developed in the future, and the like. Various protocols such as transmission control protocol/Internet protocol (TCP/IP), Ethernet, file transfer protocol (FTP), hypertext transfer protocol (HTTP) and the like may be used, and the system can be operated in a client-server configuration to permit a user to retrieve web pages from a web-based server. Any of various conventional web browsers can be used to display and manipulate data on web pages.

Although the elements of FIG. 6E are illustrated as logical block diagrams, the disclosure is not so limited. In particular, one or more of the logical boxes in FIG. 6E may be combined into a single logical box or the functionality performed by a single logical box may be divided across multiple existing or new logical boxes. Moreover, some logical boxes that are visually presented as being inside of another logical box may be moved such that they are partially or completely residing outside of that logical box. For example, while the database is visually depicted in FIG. 6E as being stored inside one or more memories in the remote device 1054, FIG. 6E contemplates that the database may be stored in a standalone data store communicatively coupled, via the communications interface, to the modules stored at the remote device 1054 and processor of the remote device 1054.

Referring to FIG. 6, in some examples, the performance of operation in a plant may be improved by using a cloud computing infrastructure and associated methods, as described in US Patent Application Publication No. US2016/0260041, which was published Sep. 8, 2016, and which is herein incorporated by reference in its entirety. The methods may include, in some examples, obtaining plant operation information from the plant and/or generating a plant process model using the plant operation information. The method may include receiving plant operation information over the Internet, or other computer network (including those described herein) and automatically generating a plant process model using the plant operation information. These plant process models may be configured and used to monitor, predict, and/or optimize performance of individual process units, operating blocks and/or complete processing systems. Routine and frequent analysis of predicted versus actual performance may further allow early identification of operational discrepancies, which may be acted upon to optimize impact.

The aforementioned cloud computing infrastructure may use a data collection platform 1002 associated with a plant to capture data, e.g., sensor measurements, which may be automatically sent to the cloud infrastructure, which may be remotely located, where it may be reviewed to, for example, eliminate errors and biases, and used to calculate and report performance results. The data collection platform 1002 may include an optimization unit that acquires data from a customer site, other site, and/or plant (e.g., sensors and other data collectors at a plant) on a recurring basis. For cleansing, the data may be analyzed for completeness and corrected for gross errors by the optimization unit. The data may also be corrected for measurement issues (e.g., an accuracy problem for establishing a simulation steady state) and overall mass balance closure to generate a duplicate set of reconciled plant data. The corrected data may be used as an input to a simulation process, in which the process model is tuned to ensure that the simulation process matches the reconciled plant data. An output of the reconciled plant data may be used to generate predicted data using a collection of virtual process model objects as a unit of process design.

The performance of the plant and/or individual process units of the plant is/are compared to the performance predicted by one or more process models to identify any operating differences or gaps. Furthermore, the process models and collected data (e.g., plant operation information) may be used to run optimization routines that converge on an optimal plant operation for a given values of, e.g., feed, products, and/or prices. A routine may be understood to refer to a sequence of computer programs or instructions for performing a particular task.

The data analysis platform 1004 may include an analysis unit that determines operating status, based on at least one of a kinetic model, a parametric model, an analytical tool, and/or a related knowledge and/or best practice standard. The analysis unit may receive historical and/or current performance data from one or a plurality of plants to proactively predict one or more future actions to be performed. To predict various limits of a particular process and stay within the acceptable range of limits, the analysis unit may determine target operational parameters of a final product based on actual current and/or historical operational parameters. This evaluation by the analysis unit may be used to proactively predict future actions to be performed. In another example, the analysis unit may establish a boundary or threshold of an operating parameter of the plant based on at least one of an existing limit and an operation condition. In yet another example, the analysis unit may establish a relationship between at least two operational parameters related to a specific process for the operation of the plant. Finally in yet another example, one or more of the aforementioned examples may be performed with or without a combination of the other examples.

The plant process model predicts plant performance that is expected based upon the plant operation information. The plant process model results can be used to monitor the health of the plant and to determine whether any upset or poor measurement occurred. The plant process model is desirably generated by an iterative process that models at various plant constraints to determine the desired plant process model.

Using a web-based system for implementing the method of this disclosure may provide one or more benefits, such as improved plant performance due to an increased ability by plant operators to identify and capture opportunities, a sustained ability to bridge plant performance gaps, and/or an increased ability to leverage personnel expertise and improve training and development. Some of the methods disclosed herein allow for automated daily evaluation of process performance, thereby increasing the frequency of performance review with less time and effort required from plant operations staff.

Further, the analytics unit may be partially or fully automated. In one or more embodiments, the system is performed by a computer system, such as a third-party computer system, remote from the plant and/or the plant planning center. The system may receive signals and parameters via the communication network, and displays in real time related performance information on an interactive display device accessible to an operator or user. The web-based platform allows all users to work with the same information, thereby creating a collaborative environment for sharing best practices or for troubleshooting. The method further provides more accurate prediction and optimization results due to fully configured models. Routine automated evaluation of plant planning and operation models allows timely plant model tuning to reduce or eliminate gaps between plant models and the actual plant performance. Implementing the aforementioned methods using the web-based platform also allows for monitoring and updating multiple sites, thereby better enabling facility planners to propose realistic optimal targets.

Figure 7A:
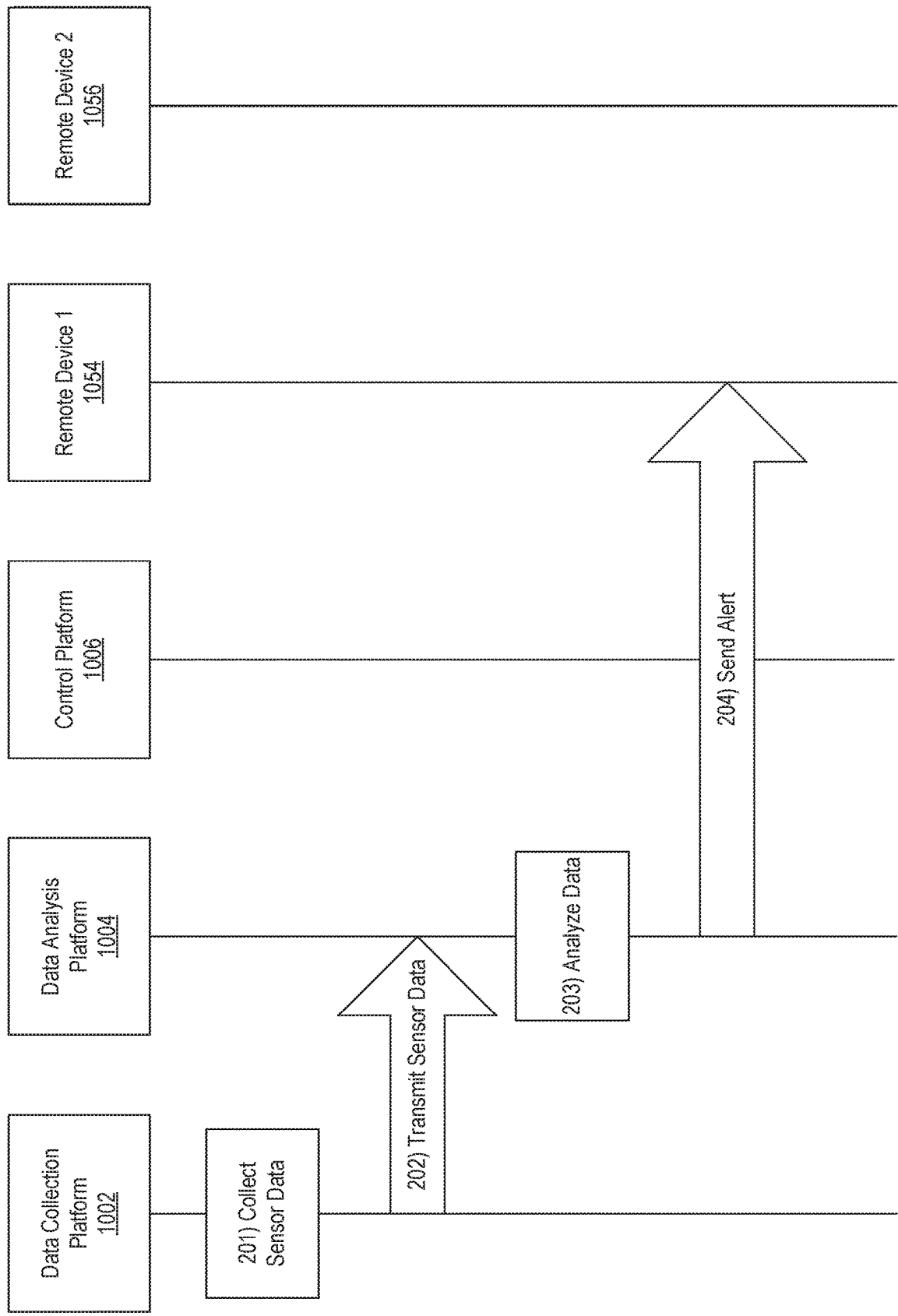
FIGS. 7A-7B depict an illustrative flow diagram of one or more steps that one or more devices may perform in controlling one or more aspects of a plant operation in accordance with one or more example embodiments.
Figure 7B:
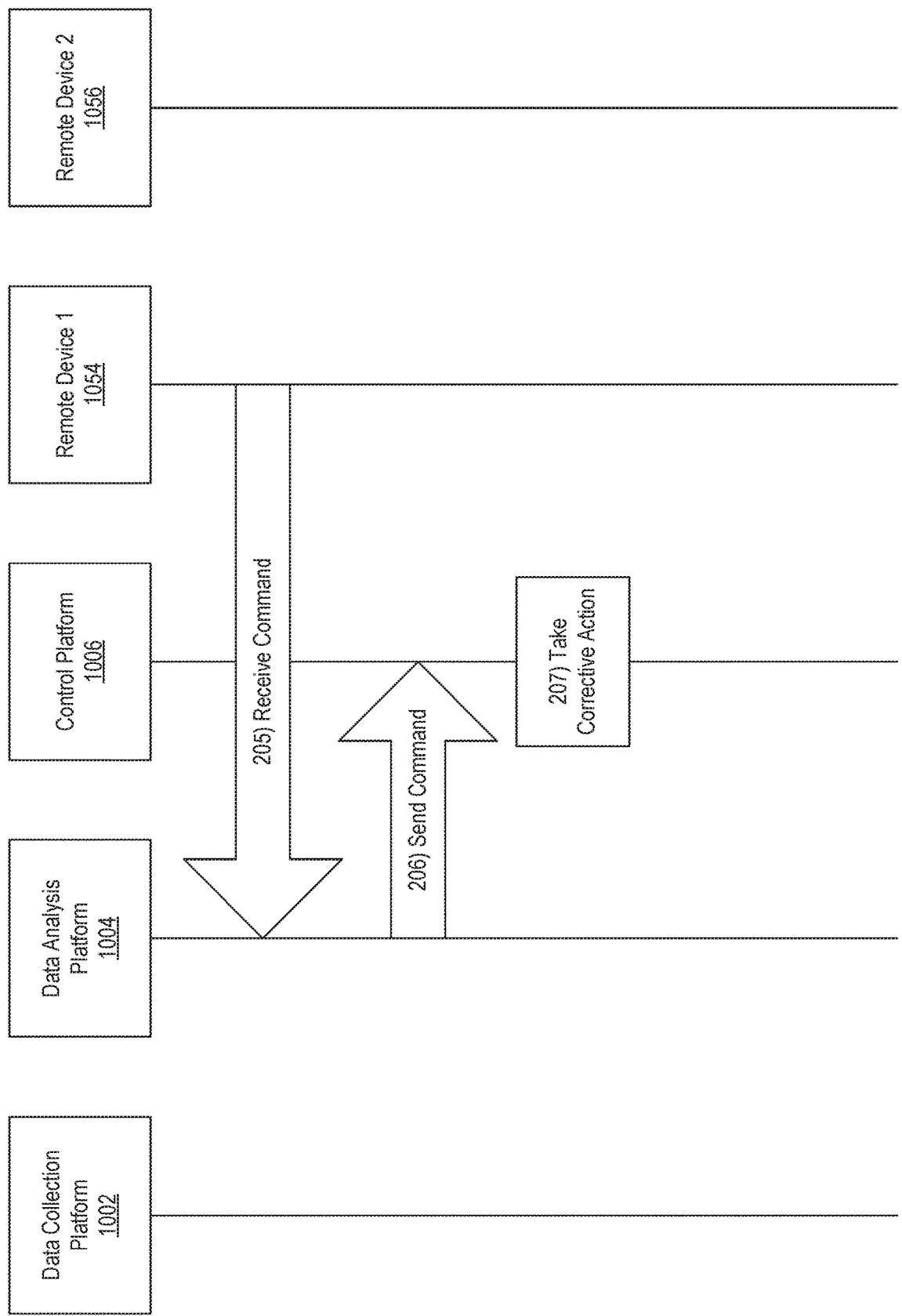

FIGS. 7A and 7B depict illustrative system flow diagrams in accordance with one or more embodiments described herein. As shown in FIG. 7A, in step 201, data collection platform 1002 may collect sensor data. In step 202, data collection platform 1002 may transmit sensor data to data analysis platform 1004. In step 203, data analysis platform 1004 may analyze data. In step 204, data analysis platform 1004 may send an alert to remote device 1054 and/or remote device 1056.

As shown in FIG. 7B, in step 205, data analysis platform 1004 may receive a command from remote device 1054 and/or remote device 1056. In some embodiments, the control platform 1006 may receive the command from remote device 1054 and/or remote device 1056. In step 206, data analysis platform 1004 may send a command to control platform 1006. In some embodiments, the command may be similar to the command received from remote device 1054 and/or remote device 1056. In some embodiments, data analysis platform 1004 may perform additional analysis based on the received command from remote device 1054 and/or remote device 1056 before sending a command to control platform 1006. In step 207, control platform 1006 may take corrective action. The corrective action may be based on the command received from data analysis platform 1004, remote device 1054, and/or remote device 1056. The corrective action may be related to one or more pieces of equipment (e.g., heat exchanger) associated with sensors that collected the sensor data in step 201.

Figure 10:
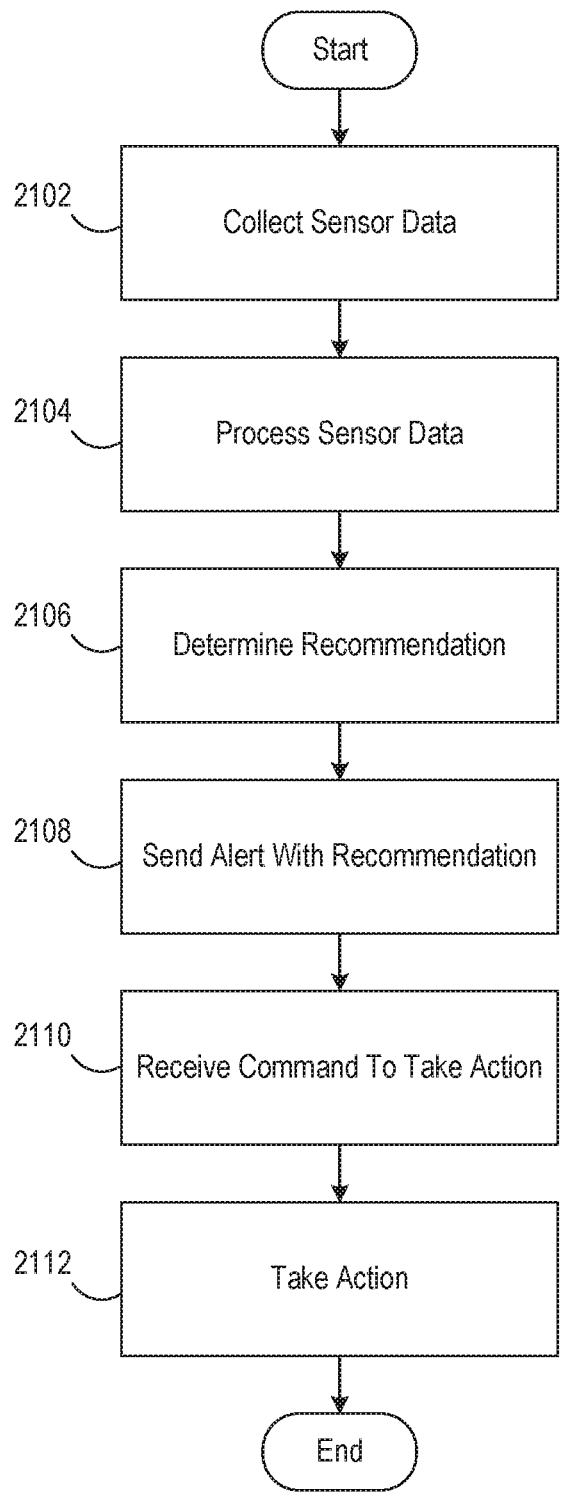
FIG. 10 depicts an illustrative flowchart of a process that one or more devices may perform in controlling one or more aspects of a plant operation in accordance with one or more example embodiments.

FIG. 10 depicts an illustrative flow diagram in accordance with one or more embodiments described herein. The flow may be performed by one or more devices, which may be interconnected via one or more networks.

First, the one or more devices may collect 2102 sensor data. The sensor data may be from one or more sensors attached to one or more pieces of equipment (e.g., a heat exchanger) in a plant. The sensor data may be locally collected and processed and/or may be locally collected and transmitted for processing. The data may be collected on a periodic basis.

After the sensor data is collected, the one or more devices may process 2104 the sensor data. The one or more devices may compare the data to past data from the one or more pieces of equipment, other pieces of equipment at a same plant, one or more pieces of equipment at a different plant, manufacturer recommendations or specifications, or the like.

After the sensor data is processed, the one or more devices may determine 2106 one or more recommendations based on the sensor data. The one or more recommendations may include recommendations of one or more actions to take based on the sensor data.

The one or more devices may send 2108 one or more alerts, which may include the determined recommendation. The one or more alerts may include information about the sensor data, about other data, or the like.

The data taken from one or more of the various sensors may be correlated with weather and environmental data to determine predictive models of potential problems in the current heat exchanger, and/or other heat exchanger used in different processes and environments.

The one or more devices may receive 2110 a command to take an action (e.g., the recommended action, an action other than the recommended action, or no action). After receiving the command, the one or more devices may take 2112 the action. The action may, in some embodiments, include one or more corrective actions, which may cause one or more changes in the operation of the one or more pieces of equipment. The corrective action(s) may be taken automatically or after user confirmation, and/or the corrective action(s) may be taken without an accompanying alert being generated (and vice-versa).

Figure 8:
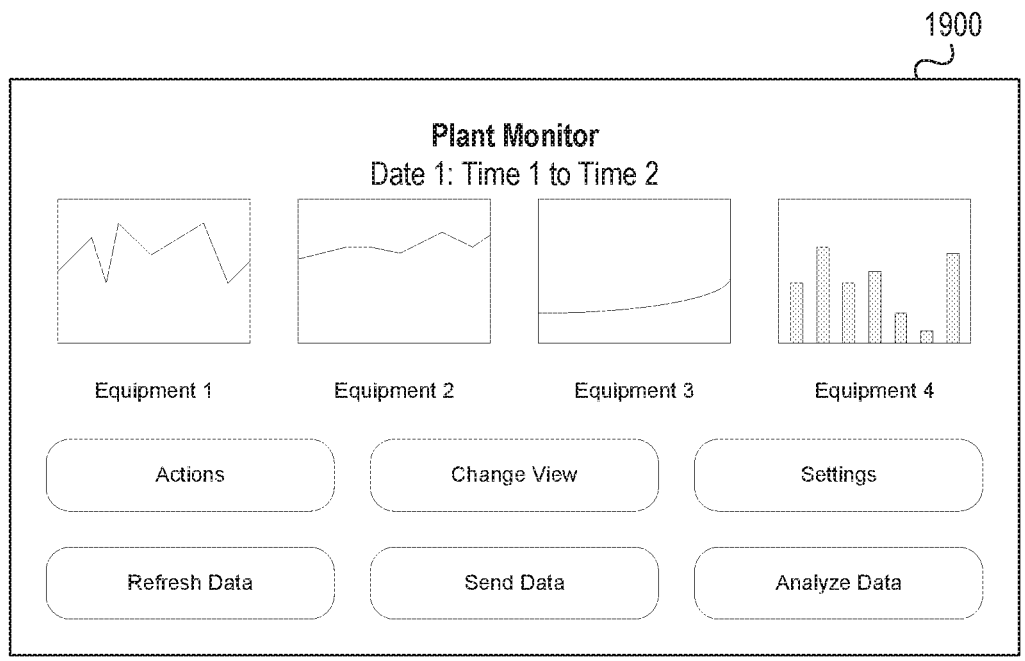
FIGS. 8-9 depict illustrative graphical user interfaces related to one or more aspects of a plant operation in accordance with one or more example embodiments.

FIG. 8 depicts an illustrative graphical user interface 1900 of an application that may be used for providing information received from one or more sensors or determined based on analyzing information received from one or more sensors, according to one or more embodiments described herein. The graphical user interface may be displayed as part of a smartphone application (e.g., running on a remote device, such as remote device 1054 or remote device 1056), a desktop application, a web application (e.g., that runs in a web browser), a web site, an application running on a plant computer, or the like.

The graphical user interface 1900 may include one or more visual representations of data (e.g., chart, graph, etc.) that shows information about a plant, a particular piece of equipment in a plant, or a process performed by a plant or a particular piece or combination of equipment in the plant. For example, a graph may show information about an operating condition, an efficiency, a production level, or the like. The graphical user interface 1900 may include a description of the equipment, the combination of equipment, or the plant to which the visual display of information pertains.

The graphical user interface 1900 may display the information for a particular time or period of time (e.g., the last five minutes, the last ten minutes, the last hour, the last two hours, the last 12 hours, the last 24 hours, etc.). The graphical user interface may be adjustable to show different ranges of time, automatically or based on user input.

The graphical user interface 1900 may include one or more buttons that allow a user to take one or more actions. For example, the graphical user interface may include a button (e.g., an "Actions" button) that, when pressed, shows one or more actions available to the user. The graphical user interface may include a button (e.g., a "Change View" button) that, when pressed, changes one or more views of one or more elements of the graphical user interface. The graphical user interface may include a button (e.g., a "Settings" button) that, when pressed, shows one or more settings of the application of which the graphical user interface is a part. The graphical user interface may include a button (e.g., a "Refresh Data" button) that, when pressed, refreshes data displayed by the graphical user interface. In some aspects, data displayed by the graphical user interface may be refreshed in real time, according to a preset schedule (e.g., every five seconds, every ten seconds, every minute, etc.), and/or in response to a refresh request received from a user. The graphical user interface may include a button (e.g., a "Send Data" button) that, when pressed, allows a user to send data to one or more other devices. For example, the user may be able to send data via email, SMS, text message, iMessage, FTP, cloud sharing, AirDrop, or via some other method. The user may be able to select one or more pieces of data, graphics, charts, graphs, elements of the display, or the like to share or send. The graphical user interface may include a button (e.g., an "Analyze Data" button) that, when pressed, causes one or more data analysis functions to be performed. In some aspects, the user may provide additional input about the desired data analysis, such as desired input, desired output, desired granularity, desired time to complete the data analysis, desired time of input data, or the like.

Figure 9:
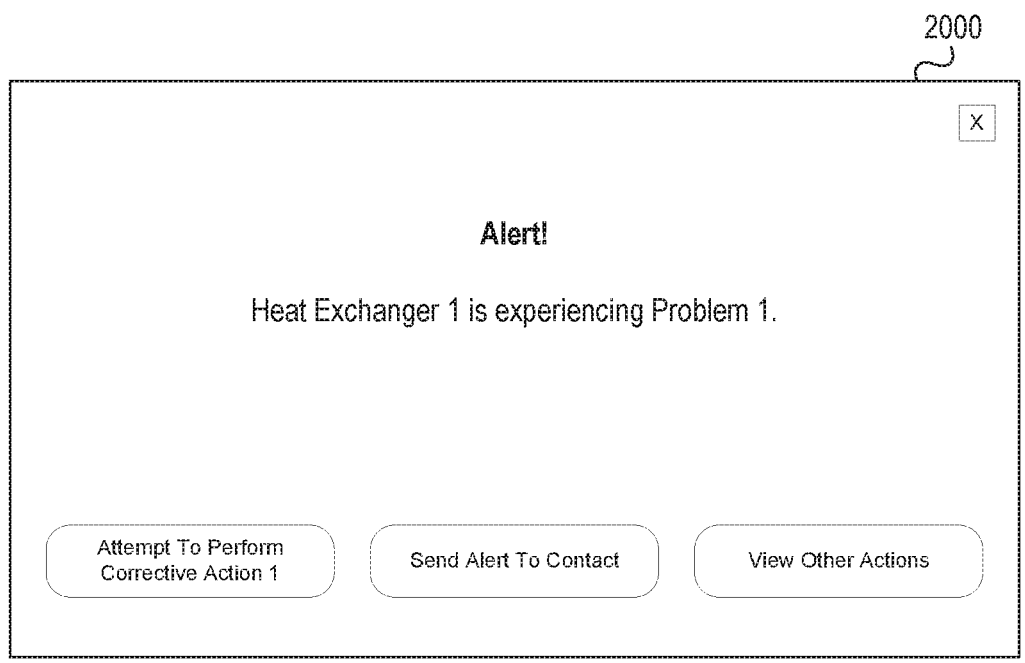

FIG. 9 depicts an illustrative graphical user interface 2000 of an application that may be used for providing alerts and/or receiving or generating commands for taking corrective action, in accordance with one or more embodiments described herein. The graphical user interface 2000 may include an alert with information about a current state of a piece of equipment (e.g., a heat exchanger), a problem being experienced by a piece of equipment (e.g., a heat exchanger), a problem with a plant, or the like. For example, the graphical user interface may include an alert that a heat exchanger is experiencing maldistribution, cross-leakage, thermal stresses, fouling, vibration, liquid lift, that pre-leakage has been detected, or another alert.

The graphical user interface 2000 may include one or more buttons that, when pressed, cause one or more actions to be taken. For example, the graphical user interface 2000 may include a button that, when pressed, causes a flow rate to change. In another example, the graphical user interface 2000 may include a button that, when pressed, sends an alert to a contact (e.g., via a remote device), the alert including information similar to the information included in the alert provided via the graphical user interface. In a further example, the graphical user interface 2000 may include a button that, when pressed, shows one or more other actions that may be taken (e.g., additional corrective actions).

Air-Cooled Heat Exchangers

Aspects of the disclosure are directed to a system that detects and corrects conditions that can affect operation of an air-cooled exchanger.

Air-cooled heat exchangers utilize air to provide cooling of a warm process stream (liquids, vapors, one-phase or two-phase streams) that flows through tube bundles. The process fluids or vapors are contained in a closed-loop tube bundles (no exposure to outside air). The bundles may be rectangular bundles. The tubes may be parallel to each other and may contain or have attached fins. The tubes may have grooves with a fin in each groove. Fins may be attached by other methods. A fan situated below the bundles may blow air up and between the bundles of tubes. A fan may also be situated above the bundle and draw or induce air up between the bundle of tubes.

Air-cooled heat exchangers may have issues due to maldistribution (of either or both the process fluid and the air flow), vibration, fouling, including fouling on fans, vibration of tubes, vibration of fans, freezing or pour point issues, and/or thermal stresses. There can be thermal stresses, as tubes are often hot at the top of the bundle and cold at the bottom. Temperature on each tube may be different. In the header box, temperature differences can break joints. Insufficient air flow can cause fouling of fins. Fins may become detached, loosen, and/or have mechanical failures. For instance, if fins are made of a metal different than the tubes, there can be differential expansion between the dissimilar materials. In addition, fin heights can make a difference in flow and thereby introduce stresses to the system.

An air-cooled heat exchanger is exposed to the environment. Hence, contaminants in the air may be monitored, such as particulates, pollutants, dust dirt, pollen, corrosive agents, and biologics.

Sensors may be used to measure temperature, pressure, and flow of the process fluids. Infrared camera mounted outside of equipment can continually take temperature measurements along different locations of the bundles and monitor temperature gradients. Temperature sensors (e.g., thermocouples) can be placed on the tubes and on the fins, at the inlet, the outlet, the center and/or at additional locations along the tubes. Pressure sensors may detect pressure drops between inlet and outlet in the header of each bundle. In an example, pressure sensors can be placed at the inlet and the outlet of each bundle. Pressure drop can indicate fouling or maldistribution. Magnetic sensors or ultrasonic sensors or other means may be used to measure flow. Position sensors may be used to monitor positions of each fin. For example, if a fin is loose or detached, then the position sensor may indicate that the fin is in a different position than the fin previously was in, which may indicate that the fin is damaged and needs to be repaired or replaced. Optical sensors may be used to monitor exterior elements of the air-cooled heat exchanger (e.g., the fins) for fouling. For example, if an optical sensor located on an outside of a fin is covered up, it may indicate that fouling is occurring, and that the fin needs to be cleaned or replaced.

Sensor information may be gathered by one or more sensors and transmitted to data collection platform. Data collection platform may transmit the collected sensor data to data analysis platform, which may be at a plant or remote from a plant (e.g., in the cloud).

Data analysis platform may analyze the received sensor data. Data analysis platform may compare the sensor data to one or more rules to determine if problems are occurring. For example, data analysis platform may determine that the deviations may indicate damage if: (1) a large change is determined over a short time frame (e.g., 10% over 3 hours), (2) a smaller change is determine over a long time frame (e.g., 3% over 10 days that increase 0.3% each day), (3) the changes in the system match the fingerprint of prior changes that were detected and the changes resulted in damage to the system, (4) the changes pass a preset threshold.

For example, data analysis platform may compare current sensor data to past sensor data from the heat exchanger, from other heat exchangers at the same plant, from other heat exchangers at other plants, from a manufacturer, or the like. Data analysis platform may determine if one or more data characteristics of the sensor data match data that may indicate problems with the air-cooled heat exchanger. Data that may indicate problems with the air-cooled heat exchanger may, alone or in a combination, be considered a fingerprint. When current sensor data matches a fingerprint of a particular condition, data analysis platform may determine that the condition is happening or potentially developing in the current system as well. Data may be collected over many years from many different locations, and data analysis platform can match the current data to fingerprints of past data or situations. Thresholds used for particular rules may change or be adjusted over time based on past fingerprints calculation tools.

From the collected data, as well as data collected from other air-cooled heat exchangers, data analysis platform may run process simulations to determine if problems are occurring or are likely to occur. One or more possible variables may be taken into account in these calculations, including temperature, pressure, flow, composition, properties of components, physical properties of fluids based on composition, fan speed, air flow. Optimal operating conditions and limits of equipment (e.g., from vendor) may be taken into account.

Data analysis platform may further run process simulations to suggest changes to flow compositions and operating parameters to avoid or limit damage. In some aspects, data analysis platform may communicate with one or more vendors regarding the results of the simulation, and receive recommendations from the vendor on how to change or optimize operation or geometry of the equipment. The results of the process simulation may further be used to determine how quickly a problem occurs, to identify one or more fingerprints for the problem, and/or identify one or more signatures for how the problem occurs. Data analysis platform may use this information to create or expand a searchable database.

In some embodiments, data from the sensors may be correlated with weather data at the plant. For example, if a rainstorm is currently happening at the plant, the surface temperature, operating temperature, another temperature, and/or a pressure of the exchanger might drop. In another example, if a drought and heat wave are currently happening at the plant, the surface temperature, operating temperature, another temperature, and/or a pressure of the exchanger might increase. The data analysis platform may determine, based on the correlation of the weather conditions to the changes in exchanger data, that the changes in the exchanger are due to weather conditions, and not, e.g., due to another problem.

In some embodiments, data from different types of sensors may be cross-checked to confirm conclusions drawn from that data, to determine data reliability, and the like. For example, temperature readings from skin thermocouples may be compared to temperature readings from a thermal imaging camera, thermal topography may be compared to photographs, or the like.

Based on the sensor data, process simulations, fingerprint analysis, and/or other data processing, data analysis platform may determine one or more recommended changes to operation of the air-cooled heat exchanger, such as decreasing temperature, pressure, or feed flow, or increasing recycle flow.

In some aspects, if air-cooled heat exchanger problems or one or more conditions that may cause air exchanger problems are detected, an alarm (e.g., a visual and/or audible alarm) may be triggered. The alarm could be an alarm at a plant, an alarm that is sent to one or more devices, an alarm on the heat exchanger, an alarm that shows on a web page or dashboard, or the like.

In some aspects, if air-cooled heat exchanger problems are detected, control platform may take one or more actions, which may be triggered, requested, or recommended by data analysis platform. Alternatively or additionally, data analysis platform may trigger an alert to one or more remote devices (e.g., remote device 1, remote device 2). The alert may include information about the air-cooled heat exchanger problems (e.g., relative temperatures, relative flows, and history of the air-cooled heat exchanger problems). The alert may provide information about one or more determined correlations between air exchanger problems and a particular operating condition or combination of operating conditions. The alert may include one or more recommendations for and/or commands causing adjustments to operating conditions, adjustments to fan speeds, flows, valves, nozzles, drains, or the like.

In some aspects, a remote device may send a command for a particular action (e.g., a corrective action) to be taken, which may or may not be based on the alert. In some aspects, data analysis platform may send a command for a particular action to be taken, whether or not an alert was sent to or a command was sent by the remote device. The command may cause one or more actions to be taken, which may mitigate air exchanger problems, prevent equipment (e.g., air exchanger) damage, avoid failure, or the like. For example, if an air exchanger problem rapidly develops, and, based on analyzing the growth rate of the air exchanger problem in view of current operating conditions, data analysis platform determines that the air exchanger problem soon will cross over a particular threshold (e.g., over a cost threshold, over a safety threshold, over a risk threshold, or the like), a command (e.g., a plant shutdown, a process shutdown, an air exchanger shutdown, a backup heat exchanger activation, or the like) may be sent in order to avoid equipment failure, catastrophic failure, air exchanger damage, plant damage, or some other damage.

Inlet air temperature may vary over season or time of day. Therefore, data analysis platform may monitor the air flow from the fan (e.g., based on air-flow sensor data). Data analysis platform may recommend or send to control platform a command to alter a fan speed based on the outside conditions. For example, fan speed and pitch of blades can be modified or diverters may be used. These modifications may be made manually (e.g., based on a recommendation) or automatically (e.g., by control platform).

If data analysis platform determines that fouling is or may be occurring, data analysis platform may recommend or send to control platform a command to wash the air exchanger bundle. Preferably this is done without shutting down the plant. An air-cooled system allows for easy access to the bundles and tubes, and a typical air-cooled heat exchanger will have two or more fans, each fan corresponding to a collection of bundles. This allows one fan to be turned off for bundle cleaning and fan service while the other fan(s) and bundles remain online.

Similarly, if evidence of effluent salts is observed, the data analysis platform may activate or recommend intermittent water wash injection on the process side to either specific bundles or all the bundles.

Similarly, if bundles are operating in parallel, data analysis platform may recommend or send to control platform a command to take one bundle offline and wash the one bundle while the other bundle is operation. If necessary, a bundle may be replaced while offline.

Data analysis platform may recommend or send to control platform a command to, depending on determinations based on the sensor data, increase or decrease the amount of flow placed over the tubes or through the tubes.

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one or more of the steps illustrated in the illustrative figures may be performed in other than the recited order, and one or more depicted steps may be optional in accordance with aspects of the disclosure.

What is claimed is:

1. A system comprising:
   a reactor;
   a heater;
   an air-cooled heat exchanger;
   a regenerator;
   a separator;
   one or more sensors associated with the air-cooled heat exchanger;
   a data collection platform comprising:
      one or more processors of the data collection platform;
      a communication interface of the data collection platform; and
      memory storing executable instructions that, when executed, cause the data collection platform to:
         receive, from the one or more sensors associated with the air-cooled heat exchanger, sensor data comprising operation information associated with the air-cooled heat exchanger;
correlate the sensor data comprising the operation information associated with the air-cooled heat exchanger with weather data corresponding to weather at a geographic location of the air-cooled heat exchanger and a time that the sensor data was collected; and
transmit the sensor data; and
a data analysis platform, comprising:
one or more processors of the data analysis platform;
a communication interface of the data analysis platform; and
memory storing executable instructions that, when executed, cause the data analysis platform to:
receive, from the data collection platform, the sensor data comprising the operation information associated with the air-cooled heat exchanger;
analyze the sensor data comprising the operation information associated with the air-cooled heat exchanger;
determine, based on correlating the sensor data with the weather data, whether the weather at the geographic location of the air-cooled heat exchanger caused fouling in the air-cooled heat exchanger;
based on determining fouling in the operating condition of the air-cooled heat exchanger, determine a recommended adjustment to the operating condition of the air-cooled heat exchanger;
cause display of the recommended adjustment to the operating condition of the air-cooled heat exchanger on a graphical user interface of a computing device; and
send a command configured to cause the recommended adjustment to the operating condition of the air-cooled heat exchanger.

2. The system of claim 1, comprising:
an air-quality sensor,
wherein the memory of the data analysis platform stores executable instructions that, when executed, cause the data analysis platform to:
receive air-quality data collected by the air-quality sensor; and
analyze the air-quality data collected by the air-quality sensor to determine a problem in the operating condition of the air-cooled heat exchanger.

3. The system of claim 1, comprising:
a fin associated with the air-cooled heat exchanger; and
a position sensor associated with the fin associated with the air-cooled heat exchanger,
wherein the memory of the data analysis platform stores executable instructions that, when executed, cause the data analysis platform to:
receive position data collected by the position sensor, the position data indicating a position of the fin associated with the air-cooled heat exchanger; and
analyze the position data collected by the position sensor to determine whether the fin associated with the air-cooled heat exchanger is in a different position than a previous position of the fin associated with the air-cooled heat exchanger.

4. The system of claim 1, comprising:
a temperature sensor,
wherein the memory of the data analysis platform stores executable instructions that, when executed, cause the data analysis platform to:
receive temperature data collected by the temperature sensor; and
analyze the temperature data collected by the temperature sensor to determine a problem in the operating condition of the air-cooled heat exchanger.

5. The system of claim 1, comprising:
a pressure sensor,
wherein the memory of the data analysis platform stores executable instructions that, when executed, cause the data analysis platform to:
receive pressure data collected by the pressure sensor; and
analyze the pressure data collected by the pressure sensor to determine a problem in the operating condition of the air-cooled heat exchanger.

6. The system of claim 5, wherein the memory of the data analysis platform stores executable instructions that, when executed, cause the data analysis platform to:
analyze the pressure data collected by the pressure sensor to determine the problem in the operating condition of the air-cooled heat exchanger based on a pressure drop between an inlet of a header of a bundle of the air-cooled heat exchanger and an outlet of the header of the bundle of the air-cooled heat exchanger.

7. The system of claim 1, comprising:
a flow sensor,
wherein the memory of the data analysis platform stores executable instructions that, when executed, cause the data analysis platform to:
receive flow data collected by the flow sensor; and
analyze the flow data collected by the flow sensor to determine a problem in the operating condition of the air-cooled heat exchanger.

8. The system of claim 7, wherein the flow sensor is a magnetic sensor.

9. The system of claim 1, wherein the memory of the data analysis platform stores executable instructions that, when executed, cause the data analysis platform to:
compare the sensor data comprising the operation information associated with the air-cooled heat exchanger to past sensor data associated with the air-cooled heat exchanger to determine if there is a deviation between the sensor data and the past sensor data greater than a threshold deviation.

10. The system of claim 1, wherein the memory of the data analysis platform stores executable instructions that, when executed, cause the data analysis platform to:
compare the sensor data comprising the operation information associated with the air-cooled heat exchanger to different sensor data associated with a different air-cooled heat exchanger of a same type as the air-cooled heat exchanger to determine if there is a deviation between the sensor data and the different sensor data greater than a threshold deviation.

11. The system of claim 1, wherein the memory of the data analysis platform stores executable instructions that, when executed, cause the data analysis platform to:
based on a problem in the operating condition of the air-cooled heat exchanger, trigger an alarm.

12. The system of claim 1, wherein the memory of the data analysis platform stores executable instructions that, when executed, cause the data analysis platform to:
compare a fingerprint of a problem in the operating condition of the air-cooled heat exchanger to a past fingerprint of a past problem in a past operating condition of the air-cooled heat exchanger to determine a severity of the problem in the operating condition of the air-cooled heat exchanger.

13. One or more non-transitory computer-readable media storing executable instructions that, when executed, cause a system to:

receive sensor data comprising operation information associated with an air-cooled heat exchanger;

correlate the sensor data comprising the operation information associated with the air-cooled heat exchanger with weather data corresponding to weather at a geographic location of the air-cooled heat exchanger and a time that the sensor data was collected;

analyze the sensor data comprising the operation information associated with the air-cooled heat exchanger;

determine, based on correlating the sensor data with the weather data, whether the weather at the geographic location of the air-cooled heat exchanger caused fouling in the air-cooled heat exchanger;

based on fouling in the operating condition of the air-cooled heat exchanger, determine a recommended adjustment to the operating condition of the air-cooled heat exchanger;

cause display of the recommended adjustment to the operating condition of the air-cooled heat exchanger on a graphical user interface of a computing device; and send a command configured to cause the recommended adjustment to the operating condition of the air-cooled heat exchanger.

14. The one or more non-transitory computer-readable media of claim 13, storing executable instructions that, when executed, cause the system to:

receive first sensor data comprising first flow data measured by a first flow sensor associated with a first passage along a flow length associated with the air-cooled heat exchanger, the first flow data associated with the first passage along the flow length associated with the air-cooled heat exchanger;

receive second sensor data comprising second flow data measured by a second flow sensor associated with a second passage along the flow length associated with the air-cooled heat exchanger, the second flow data associated with the second passage along the flow length associated with the air-cooled heat exchanger;

determine whether a difference between the first flow data associated with the first passage and the second flow data associated with the second passage is greater than a threshold;

correlate the difference between the first flow data associated with the first passage and the second flow data associated with the second passage with weather data corresponding to weather at a geographic location of the air-cooled heat exchanger and a time that the sensor data was collected;

determine, based on correlating the difference between the first flow data associated with the first passage and the second flow data associated with the second passage with the weather data, whether the weather at the geographic location of the air-cooled heat exchanger caused fouling in the air-cooled heat exchanger; and based on fouling in the operating condition of the air-cooled heat exchanger, determine a recommended adjustment to the operating condition of the air-cooled heat exchanger.

15. A method comprising:

receiving, by a data analysis computing device, sensor data comprising operation information associated with an air-cooled heat exchanger;

correlating the sensor data comprising the operation information associated with the air-cooled heat exchanger with weather data corresponding to weather at a geographic location of the air-cooled heat exchanger and a time that the sensor data was collected;

determining, based on correlating the sensor data with the weather data, whether the weather at the geographic location of the air-cooled heat exchanger caused fouling in the air-cooled heat exchanger;

based on fouling in the air-cooled heat exchanger, determining, by the data analysis computing device, a recommended adjustment to the operating condition of the air-cooled heat exchanger;

displaying the recommended adjustment to the operating condition of the air-cooled heat exchanger on a graphical user interface of a computing device; and sending, by the data analysis computing device, a command configured to cause the recommended adjustment to the operating condition of the air-cooled heat exchanger.

16. The method of claim 15, comprising:

correlating air quality data collected by an air-quality sensor associated with the air-cooled heat exchanger with weather data corresponding to weather at a geographic location of the air-cooled heat exchanger to determine whether the weather at the geographic location of the air-cooled heat exchanger caused fouling in the air-cooled heat exchanger.

17. The method of claim 15, comprising:

causing, by the data analysis computing device, display of the recommended adjustment to the operating condition of the air-cooled heat exchanger on a graphical user interface of a computing device.

* * * * *